United States Patent
Foster et al.

(10) Patent No.: US 7,229,838 B2
(45) Date of Patent: *Jun. 12, 2007

(54) MEMS ACTUATOR AND METHOD OF MANUFACTURE FOR MEMS PARTICLE SORTING DEVICE

(75) Inventors: John S. Foster, Santa Barbara, CA (US); John C. Harley, Santa Barbara, CA (US); Steven H. Hovey, Goleta, CA (US); Richard T. Martin, Goleta, CA (US); Hung D. Nguyen, Los Angeles, CA (US); Paul J. Rubel, Santa Barbara, CA (US)

(73) Assignee: Innovative Micro Technology, Goleta, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/260,367

(22) Filed: Oct. 28, 2005

(65) Prior Publication Data
US 2006/0062698 A1    Mar. 23, 2006

Related U.S. Application Data

(63) Continuation-in-part of application No. 10/978,947, filed on Nov. 1, 2004, which is a continuation-in-part of application No. 10/189,607, filed on Jul. 7, 2002, now Pat. No. 6,838,056.

(51) Int. Cl.
*G01N 1/10* (2006.01)
*G01N 21/64* (2006.01)

(52) U.S. Cl. .......................... 436/180; 436/43; 436/46; 436/63; 436/149; 436/164; 436/165; 436/172; 422/82.01; 422/82.05; 422/82.08; 422/100; 435/29; 435/30; 435/287.1; 435/288.3; 435/288.4; 435/288.5; 435/288.7; 209/3.1; 209/552; 209/576

(58) Field of Classification Search .................. 436/43, 436/46, 63, 149, 150, 164, 165, 172, 177, 436/180; 422/68.1, 73, 82.01, 82.05, 82.08, 422/100, 101, 103; 435/29, 30, 287.1, 288.3–288.5, 435/288.7; 209/3.1, 552, 576
See application file for complete search history.

(56) References Cited

U.S. PATENT DOCUMENTS 5,837,200 A    11/1998 Diessel et al.

(Continued)

FOREIGN PATENT DOCUMENTS

WO    WO 01/19516    3/2001

OTHER PUBLICATIONS

Gawad et al. Lab on a Chip, vol. 1, 2001, pp. 76-82.
Blankenstein et al. Biosensors and Bioelectronics, vol. 13, Nos. 3-4, 1998, pp. 427-438.
Fu et al. Analytical Chemistry, vol. 74, No. 11, Jun. 1, 2002, pp. 2451-2457.
Baechi et al. Sensors and Actuators A, vol. 95, Jan. 1, 2002, pp. 77-83.

*Primary Examiner*—Maureen M. Wallenhorst
(74) *Attorney, Agent, or Firm*—Jaquelin K. Spong

(57) ABSTRACT

A micromechanical particle sorting chip uses an actuator divided into two parts to direct a component of interest into one of a plurality of possible exit paths, based on detection of a fluorescent signal emanating from the component of interest. The two-part actuator may include a force-generating portion and a microactuator portion. The microactuator portion may be disposable, whereas the force-generating portion may be reuseable. By bringing the force-generating portion into proximity to the microactuator portion, the microactuator is induced to move, thereby separating the component of interest from the rest of the fluid stream. The force-generating portion and the microactuator portion may be optimized and fabricated separately, thereby leading to faster, more reliable and less expensive particle sorting.

24 Claims, 18 Drawing Sheets

U.S. PATENT DOCUMENTS

| | | |
|---|---|---|
| 5,971,355 A | 10/1999 | Biegelsen et al. |
| 6,303,885 B1 | 10/2001 | Hichwa et al. |
| 6,593,749 B2 | 7/2003 | Foster et al. |
| 6,692,952 B1 | 2/2004 | Braff et al. |
| 6,791,694 B2 * | 9/2004 | Pezeshki ..................... 356/519 |
| 6,838,056 B2 * | 1/2005 | Foster ........................ 422/100 |

* cited by examiner

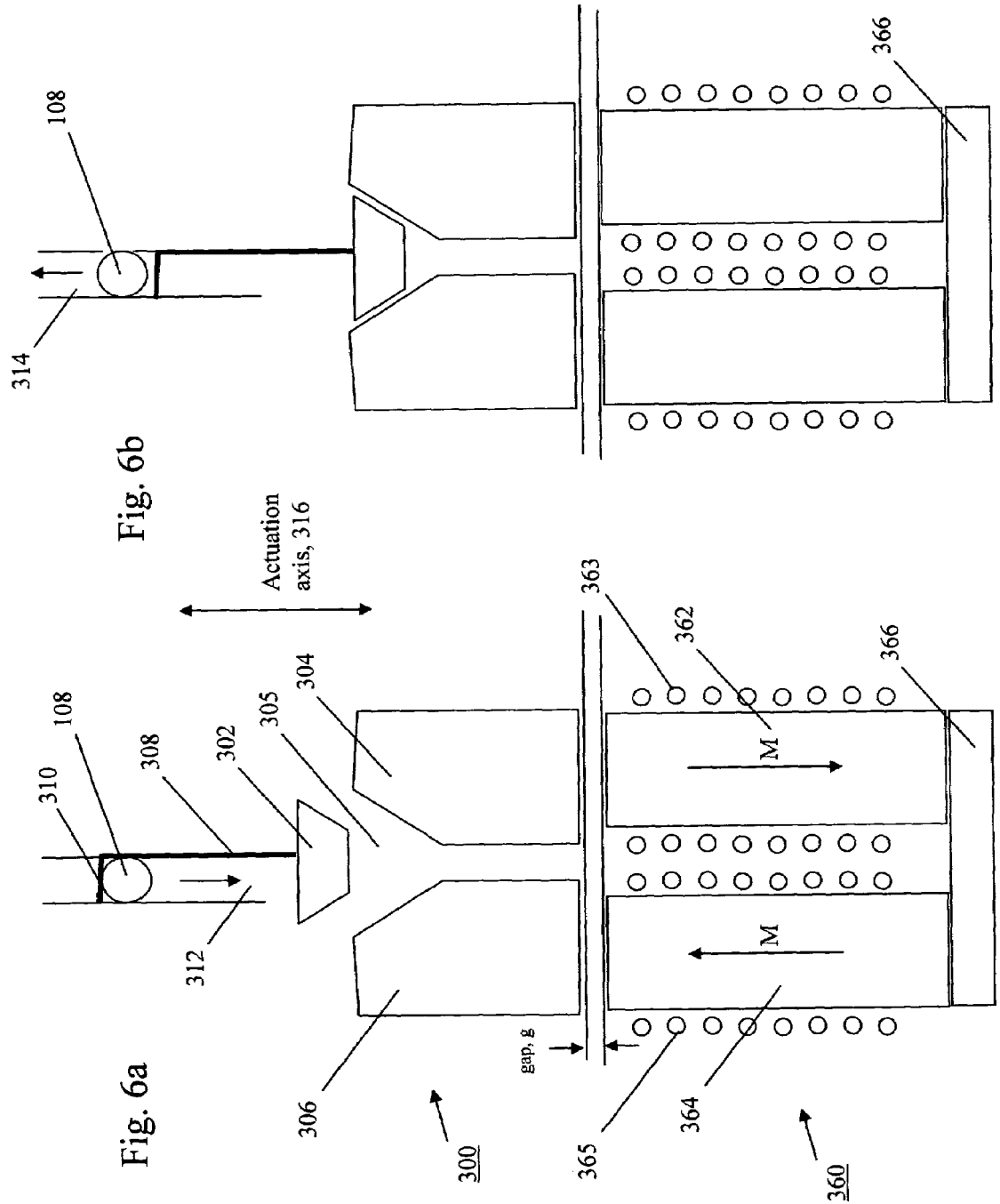

MEMS ACTUATOR AND METHOD OF MANUFACTURE FOR MEMS PARTICLE SORTING DEVICE

CROSS REFERENCE TO RELATED APPLICATIONS

This U.S. Patent application is a continuation-in-part of U.S. patent application Ser. No. 10/978,947, filed Nov. 1, 2004, which is a continuation-in-part of U.S. patent application Ser. No. 10/189,607 filed Jul. 7, 2002, now U.S. Pat. No. 6,838,056. Each of these applications is incorporated herein by reference in its entirety for all purposes.

STATEMENT REGARDING FEDERALLY SPONSORED RESEARCH

Portions of the present invention were made with U.S. Government support under DARPA Grant No. DAMD17-02-2-0067. The government may have certain rights in this invention.

STATEMENT REGARDING MICROFICHE APPENDIX

Not applicable.

BACKGROUND

This invention relates to the sorting of particles, such as biological cells, from a fluid sample. More particularly, this invention relates to a microelectromechanical systems (MEMS) particle sorting chip used to sort a component of interest from the rest of the fluid sample.

Many new therapies for cancer patients relate to enabling them to better withstand the challenge made to their bodies by the chemotherapies. In particular, it has recently been found that the inability of some patients to cope with chemotherapies has to do with the destruction of hematopoietic stem cells (HSCs), as ancillary damage of the chemotherapy. HSCs are the progenitor cells found in bone marrow, peripheral blood and many lymphoid organs. HSCs are responsible for generating the immune system components, such as T-cells, as well as the vital components of blood. When HSCs are destroyed in sufficient numbers, it becomes difficult for patients to replace blood cells, resulting in anemia often suffered by patients. The destruction of HSC's is also a leading cause of death in radiation victims, as the progenitor cells are destroyed, thereby destroying the ability to regenerate the vital components of the blood and immune systems.

Recent research has indicated however that if the human hematopoietic stem cells are removed from the patients' bodies prior to their receiving chemotherapy, and then replaced after the chemotherapy, the human hematopoietic stem cells are shielded from the effects of the chemotherapy. By reinfusing the human hematopoietic stem cells after the chemotherapy is finished, the patients' ability to regenerate their blood cells is regained and their resilience to the therapy is greatly enhanced. As a result, higher dosages of the chemotherapy can be administered to patients with better chances of diminishing the viability of the cancer cells, and yet the patients are able to regraft their blood-forming HSCs, which have been protected from exposure to the chemotherapy.

Until recently, the standard treatment for patients requiring blood-forming system reconstitution after chemotherapy was a bone marrow transplant (BMT). Bone marrow transplants require up to 100 withdrawals of marrow from the hip bone by large needles and the subsequent reinfusion of large volumes of cells and other fluid. These procedures are highly invasive, cumbersome, expensive and pose additional risks to the patient.

Mobilized peripheral blood (MPB), which accomplishes the same post-chemotherapy reconstitution with less trauma to the donor, can be generated in most patients by injecting a granulocyte colony-stimulating factor (G-CSF) that causes the body to produce a sufficient quantity of hematopoietic stem cells (HSCs). These cells migrate from the bone marrow to the blood, from which they are harvested in a sufficient quantity in a single 2-4 hour session that only requires vein access.

Both the bone marrow extractions and mobilized peripheral blood from cancer patients contain the hematopoietic stem cells necessary for reconstitution; however, they also contain large numbers of cancer cells, which are reinfused into the patient along with the human hematopoietic stem cells after the chemotherapy treatment. Logic and an increasing body of literature suggest that this reintroduction of cancer cells is one cause of the limited survival improvement associated with high dose chemotherapy and cell transplant.

Therefore, technology was developed to obtain highly purified non-cancerous HSCs from mobilized peripheral blood; i.e., the purification process eliminates the cancer cells, but retains the healthy stem cells necessary for reconstitution. The purification process also reduces the transfusion volume to less than 0.1 ml, in contrast to the 500-1500 ml of cells in fluid volume for BMT and MPB. The purification process is performed by flow cytometry, which separates the constituents of a fluid sample mixture according to fluorescence detected from the constituents. Purity of the resulting HSC product was 95% by this method, with no detectable cancer cells, and further details of the methodology can be found in Negrin et al., "Transplantation of Highly Purified $CD34^+Thy-1^+$ Hematopoietic Stem Cells in Patients with Metastatic Breast Cancer", Biology of Blood and Marrow Transplantation 6:262-271 (2000). For patients undergoing this HSC reinfusion treatment, the 5-year survival rate for women with advanced metastatic breast cancer jumped from 5% to about 50%.

Another application for HSC sorting is protection against nuclear radiation effects. The procedure would be to sort HSCs from individuals who potentially could be exposed at some later date to nuclear radiation. The human hematopoietic stem cells are frozen and can survive in that state essentially forever. If the individual is exposed, as could be the case in a nuclear plant accident or warfare, the human hematopoietic stem cells are then shipped to the patient's location, rapidly thawed, and then re-inserted into the patient. This procedure has been shown to save animals exposed to otherwise lethal doses of radiation.

However for these treatments to become practical, it must be learned how to sort large quantities of viable hematopoietic stem cells from the other constituents of the blood, with high concentration and high purity. An estimate of the number of stem cells required is $4 \times 10^6$ stem cells/kg body weight. The present separation process, flow cytometry, uses a high-pressure nozzle to separate tiny droplets containing the cells. The cell suspension is brought to the nozzle assembly under positive pressure, and introduced to the center of the sheath flow. The properties of fluid laminar flow focus the cell suspension into a single file, which is confined to the center of the fluid jet. Droplets are formed as the fluid exits the nozzle, and the droplets pass through one or more laser beams, which irradiate the cells and excite fluorescent markers with which the cells are tagged. The droplets are then given an electric charge to separate the droplets containing HSCs from those containing other constituents of the blood, as detected by fluorescence of the tagged molecules. The droplets are separated by passing them between a pair of electrostatic plate capacitors, which deflect the charged droplets into a sorting receptacle. The time-of-flight of the droplet through these stages requires careful calibration so that the sorting efficiency and effectiveness can be optimized.

Among the difficulties with the process is speed, as throughputs are limited to about 40,000 events per second. The rate is limited by the amount of pressure that the cells can withstand without damaging their viability, and the flow rate is proportional to the pressure. The fluidic settings which control the conditions of operation of the flow cytometers are interrelated. The nozzle diameter, system pressure and droplet frequency are independently set, whereas the jet velocity is related to the system pressure and nozzle diameter. Therefore the droplet time-of-flight must be set by empirical calibration with a standard sample. Therefore, not only are the systems themselves quite expensive, they require trained engineering staff to operate effectively. And lastly, contamination of the vessels with old sample tissue is a problem, as the equipment is difficult to sterilize. Decontamination issues encourage the use of disposable vessels, for which these machines are presently not designed. The high pressures used in the machines favor permanent fixturing of the plumbing in the tools. Also the careful alignment required of the receptacles with the trajectories of the droplets favors the permanent installation of the receptacles. About 7000 such systems exist worldwide today, and tend to be research tools rather than production equipment which can be used for clinical sorting in treating patients.

SUMMARY

Therefore a need exists for a separation technique that solves throughput, cost, and disposability issues associated with present methods. This disclosure describes a novel device and method based on microelectromechanical systems (MEMS). MEMS devices are micron-sized structures which are made using photolithographic techniques pioneered in the semiconductor processing industry. Due to their small size and the batch fabrication techniques used to make the structures, they are capable of massive parallelism required for high throughput. These same features make them relatively inexpensive to fabricate, so that a disposable system is a realistic target for design.

The MEMS particle sorting chip described herein has a fluid channel defined in an optically transparent substrate, and a plurality of MEMS actuators disposed beneath a channel formed between the fluid channel and a plurality of exit paths. A particle of interest is detected by irradiating a fluid stream in the fluid channel, and detecting the resulting fluorescence emanating from the particle of interest. When a particle of interest is detected, the MEMS actuator is activated, which closes one exit path and opens another, thereby directing the particle of interest into a sort/save reservoir, rather than a waste/return reservoir.

A primary figure of merit for the MEMS particle sorter described herein is throughput, which depends strongly on the speed of the actuator. In order to increase the actuator speed, the actuator may be an electromagnetic actuator made in two portions, an actuator body portion and a force-generating portion. Each of the pieces may be optimized independently, and the actuator body portion may be disposable whereas the force-generating portion may be reuseable. The actuator body portion may include a magnetizable portion attached to the actuator rigid body, which extends and retracts in response to the energizing of a pair of coils in the force-generating portion. The magnetizable portion interacts with a pair of stationary magnetic poles, which induce the motion in the actuator rigid body via the magnetizable portion.

The MEMS particle sorting chip may be applied to sorting a component of interest from the rest of a fluid sample, for example, separating human hematopoietic stem cells from a blood sample. The MEMS particle sorting chip may include at least one fluid channel formed above a micromechanical actuator, wherein the actuator is formed in two pieces, an actuator body portion and a force-generating portion. The actuator may be disposed to act at a point within the fluid channel, to direct a particle into one of a plurality of possible exit paths.

BRIEF DESCRIPTION OF THE DRAWINGS

The present invention will be understood more fully from the following detailed description, and from the accompanying drawings, which however, should not be taken to limit the invention to the specific embodiments shown but are for explanation and understanding only.

FIG. 6a shows the two-piece actuator in the extended position; FIG. 6b shows the two-piece actuator in the retracted position;

DETAILED DESCRIPTION

Figure 1:
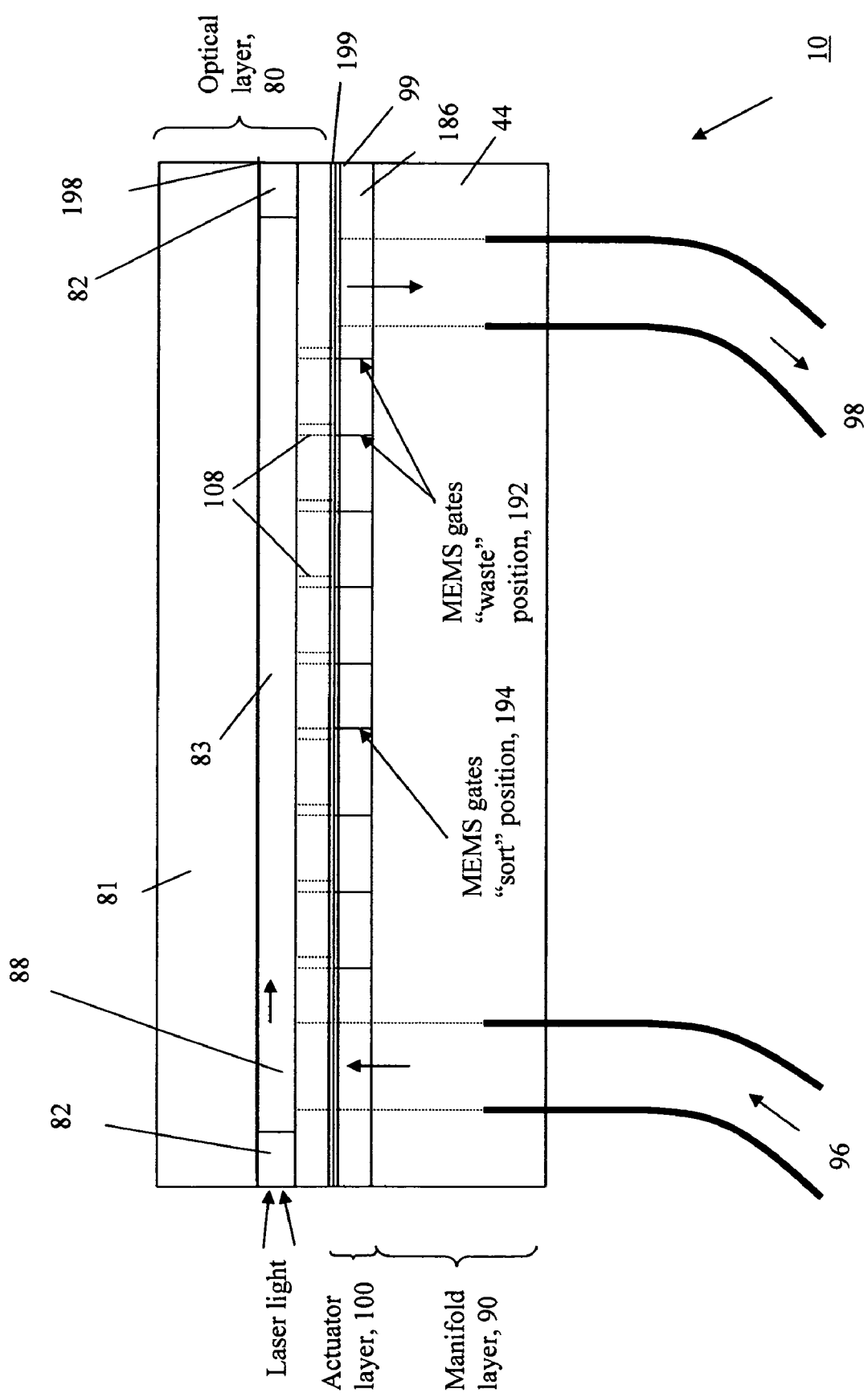
FIG. 1 is a simplified side view of the MEMS particle sorting chip, showing the light channel layer and reflective layers in detail.

The systems and methods set forth herein are described with respect to a particular embodiment, that of a cell sorter for sorting particular cells from a sample of human blood. However, it should be understood that the systems and methods may be applicable to a wide range of sorting applications, wherein it is desired to separate a particular component of interest from a remainder of a suspending fluid.

The MEMS device may be an array of parallel inlet channels fabricated in a wafer, wherein the 25 µm diameter of each channel is just large enough to allow the passage of a hematopoietic stem cell. (Hematopoietic stem cells are typically between 5 and 10 um in diameter.) At the exit from each parallel channel is an independent valve/actuator. The actuator directs the cells individually into one of two of different possible pathways, which are microfluidic channels etched into the wafer, beneath the parallel channels. The situation is shown schematically in FIG. 1. The figure shows the application of the device to the separation of the components of human blood, in this case the separation of hematopoietic stem cells (HSCs) from a fluid mixture of other cells. The actuator separates the sample stream into one of two manifolds, depending on the detection of a laser-induced fluorescence signal or multiple signals, depending on the fluorescent markers used. The presence of a fluorophore or multiple fluorphores may indicate that a human hematopoietic stem cell is detected, and the actuator may direct the cell into a stem cell manifold with its stem cell receptacle. The receptacle may contain a cushion of fresh serum for sustaining viability of the cells collected.

The use of fluorescent markers to tag biological cells is known in the art. A wide variety of fluorescent markers exist which may be conjugated as labels to antibodies specific to cellular markers which identify particular sets and subsets of cells. Fluorescent markers which are available include fluorescein, Texas Red, phycobiliproteins, cyanine derivatives and rhodamine. For example, Negrin et al. ("Transplantation of Highly Purified CD34+Thy-1+ Hematopoietic Stem Cells in Patients with Metastatic Breast Cancer", Biology of Blood and Marrow Transplantation 6:262-271 (2000)) reported that simultaneous detection of antigens CD34 and Thy-1 have good correlation to the presence of human hematopoietic stem cells. The lack of fluorescence indicates the cell is another constituent of the mixture, and not the tagged component. The occurrence of fluorescence indicates that the component of interest is present. In the case of detection of multiple fluorescent markers simultaneously, in some cases more than one laser may be used to excite the markers.

The sample cells may be dispersed in any convenient medium which can maintain viability such as phosphate-buffered saline, containing 0.1% to 0.5% fetal calf serum. The cells may have been subjected to pre-treatment, such as removal of cells by filtering, centrifugation, affinity separation or other technique which provides enrichment of the population of cells of interest. In addition, the cells may be diluted to avoid cells being concentrated too close to each other. The fluid mixture is then introduced to the MEMS device 10 under positive pressure, through the sample inlet via 96, and out through the outlet via 98. The positive pressure is chosen to select the proper flow rate through the MEMS chip 10, and can be set and fixed for the duration of the use of the chip 10. The MEMS chip 10 may include an optical cover 81 which is a barrier to the fluid mixture as well as an optically transparent element which allows the fluorescent signals to leave the chip and be detected outside the chip. A spacer layer 82 may separate optical cover 81 from the actuator layer 100, and define the thickness of the channel through which the fluid mixture flows before it enters one of the parallel channels, 108. Alternatively, an optically transparent layer 88 may be an optically transparent solid layer, with fluid channels defined therein, in which case, the spacer layers 82 may not be needed.

As the fluid mixture enters through the inlet via, it may flood the optically transparent layer 88 which lies between the optical cover 81 and the active layer substrate 44. Although optically transparent layer 88 is depicted in FIG. 1 as a simple void flooding the opening of each parallel channel 108 in parallel, it should be understood that optically transparent layer 88 may also include a plurality of well-defined fluid paths formed in the optically transparent layer 88. In this case, the fluid path may route a portion of the flow from sample input 96 to each one of the parallel channels 108, for example. The optically transparent layer 88 may also include optical elements to further focus the light in the plane of the optically transparent layer 88, as described further in co-pending U.S. patent application Ser. No. 11/196,291, incorporated by reference herein in its entirety. Optically transparent layer 88 may be sandwiched between two reflecting layers, light reflecting layers 198 and 199. The function of the optically transparent layer 88 is to guide laser light in a quasi-two-dimensional sheet, exposing the cells in the fluid mixture only before the cells fall into the parallel channels 108. The fluid mixture flows from the optically transparent layer 88 into the parallel channels 108. The parallel channels 108 may have been formed under the optically transparent layer 88 by lithographic patterning and etching, and provide a defined region 108 for delivering the fluid stream to the MEMS actuator layer 186. In optically transparent layer 88, the cells interact with the laser beam, and the cells of interest, which have been appropriately tagged with fluorescent markers, fluoresce as a result. The fluorescence is detected outside the MEMS chip 10 and the fluorescing cell is mechanically separated from the other cells in the mixture, in the MEMS actuator layer 186. The valve labeled 194 is in the sort/save position corresponding to the presence of a human hematopoietic stem cell, whereas the valves labeled 192 are in the waste/return position.

Figure 2:
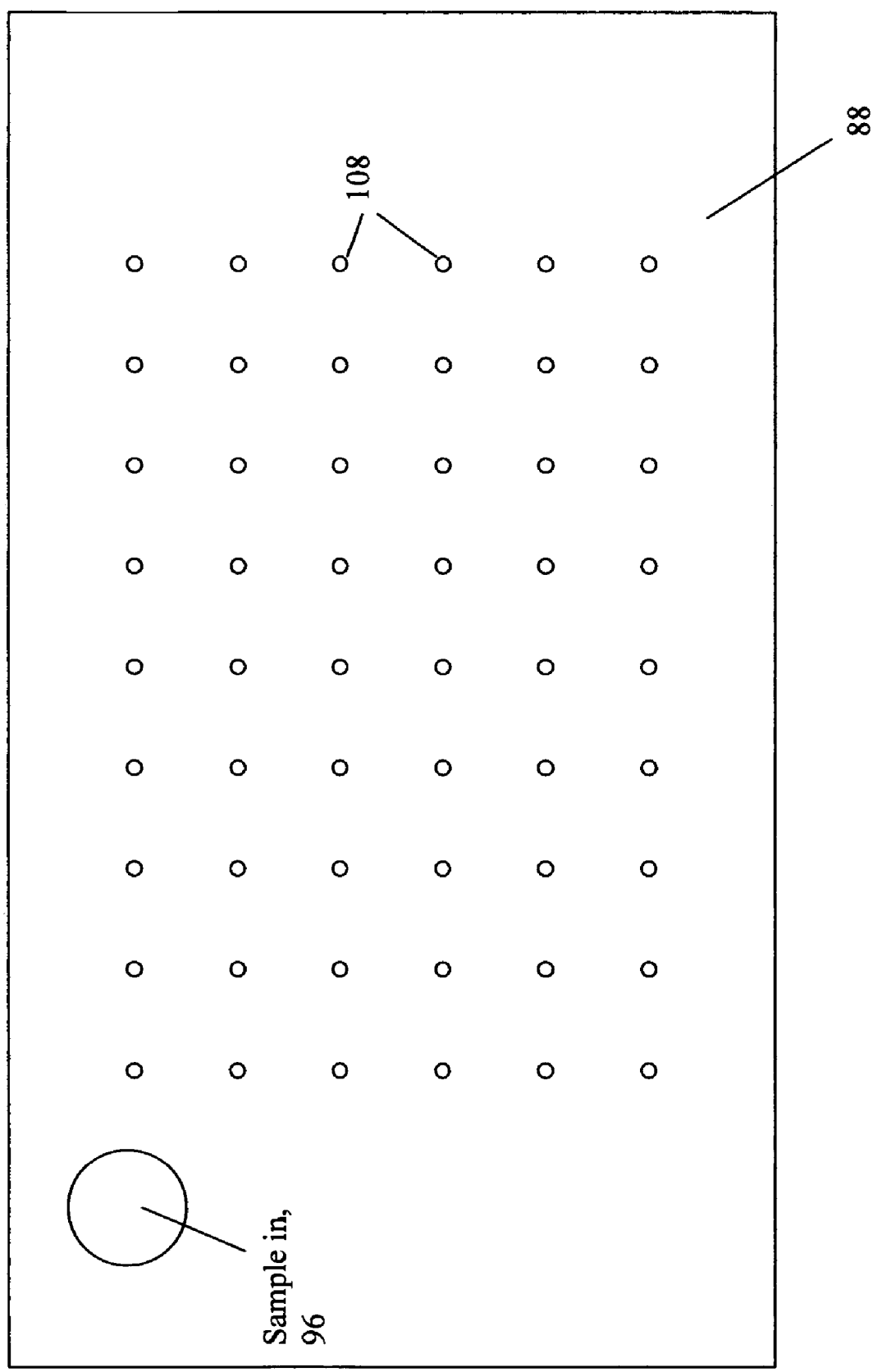
FIG. 2 is a plan view of the top surface of the MEMS particle sorting chip, showing the optically transparent light channel layer, as seen through the optical cover.

A top view of optically transparent layer 88 is shown in detail in FIG. 2, including the parallel channels, 108. The sample mixture is delivered to the top surface of FIG. 2 by the sample inlet via, 96, from which it filters down through the parallel channels 108 to the actuator/manifold layer. As with FIG. 1, optically transparent layer 88 is depicted as a simple void, although it should be understood that optically transparent layer 88 may also include well-defined channels feeding each of the parallel channels 108 with fluid from the sample input 96. As shown in FIG. 2, the optical layer may include an n×m array of parallel channels, where n and m are, for example 32. Alternatively, as described further below, the optical layer, as well as the corresponding actuator and manifold layers, may be a one-dimensional array, for example, a 1×32 array of parallel channels 108. The manifold layer 90 and actuator layer 100 are shown in plan view in FIG. 3, and they lie just beneath the optical layer 80.

Figure 3:
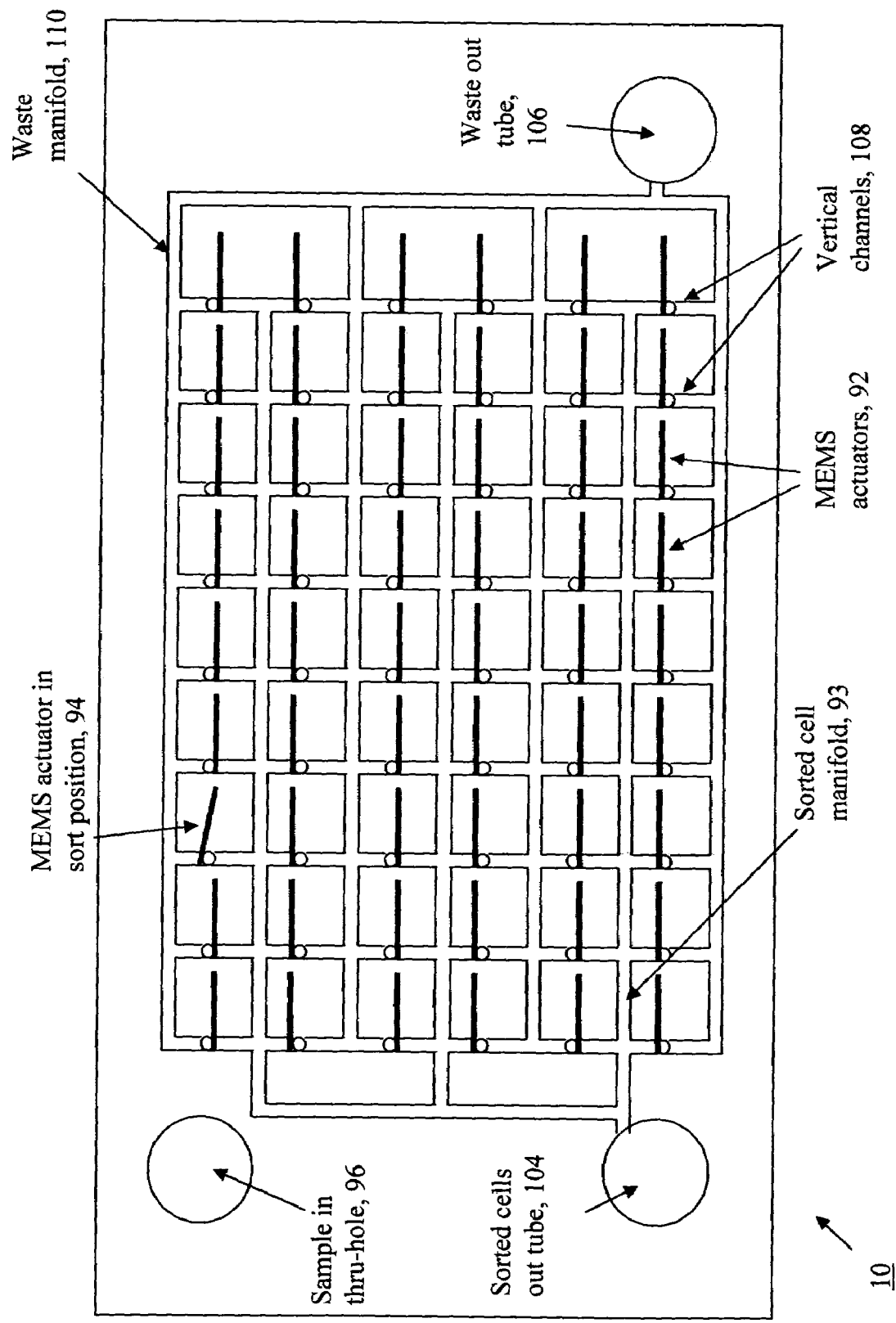
FIG. 3 is a plan view of the actuator/manifold layer of the MEMS particle sorting chip, showing the sorting manifolds.

The actuators are shown diagrammatically as the plurality of structures 192, lying at the exit of each parallel channel. As in FIG. 1, each of the actuators 192 shown is in the "waste" or "sort/save" positions, directing the cells into the waste manifold 110, with the exception of actuator 194, which is in the sort/save position. This actuator directs a fluorescing cell into the stem cell manifold 93, and the remaining actuators 192 direct non-fluorescing cells into the waste manifold 110. After being properly herded into the stem cell manifold, the cell follows the fluid stream under positive pressure, until it reaches the stem cell out tube 104 leading to the stem cell receptacle, or the waste out tube 106 leading to the waste receptacle if it is a non-fluorescing cell. The dual manifolds have been patterned in the MEMS substrate, by lithographic means, as is shown in FIG. 3. The manifolds may be sealed at the top by a top layer 99, which may be a eutectic or polymer bonding layer, and may lie between bottom light reflecting layer 199 and the MEMS actuator layer 186.

The timing of fluorescence detection, actuation and actuation back to the nominal position 192 is important so as to allow only the fluorescing cell to be sorted and minimize the chance that an errant, non-fluorescing cell be sorted mistakenly. In the nominal case, the flow rate through each channel is roughly 0.2 meter per second. Before the cell enters the parallel channel 108, it is illuminated by the laser light and begins fluorescing. The fluorescing light is detected in the first 100-200 us, and the actuator is immediately (with small computer/controller delay of only tens of microseconds) moved into position shown as sort position 194. This actuation takes approximately 100 us. Therefore, the actuator is in the sort position just as the cell is approaching the MEMS actuator layer 186. MEMS actuator layer 186 is also approximately 30 um thick. After actuation from position 192 to 194, the actuator pauses in the sort position for only 100 us, and then returns to the default position 192. In one embodiment, the actuator can move back by the restoring force of a hingedly mounted spring. In another embodiment, it is actively actuated, back to the default position 192.

In order to maximize the flow of the fluid mixture without excessive pressures, the MEMS chip utilizes a large number of parallel channels 108 flowing through the plane of the wafer as well as across the plane of the wafer. The parallel channels 108 may be formed in a thin (about 5 µm) layer of silicon, for example, which is disposed between the optically transparent layer 88 and the actuator layer 186. The large number of short path, parallel channels 108 through the wafer has the advantage that very large pressure gradients are not needed to obtain reasonable flow rates. The device is designed so that the dominant pressure drop is generated in the parallel channel region 108 only, and care is taken to provide a uniform pressure head preceding the parallel channels 108 and a minimum back pressure after the actuator region as the flow opens up into the larger manifolds. The device also does not need to create or manipulate a fine spray of droplets; instead the flow is continuous. With the actuator acting as a low inertia knife-edge gate valve, relatively low forces are needed to perform the sorting. This keeps the sample rate high with the reasonable voltages applied, less than 10 V. The tool is designed to be a low cost, special purpose machine sorting into two buckets only, but the concept is extendable to other applications.

Figure 4:
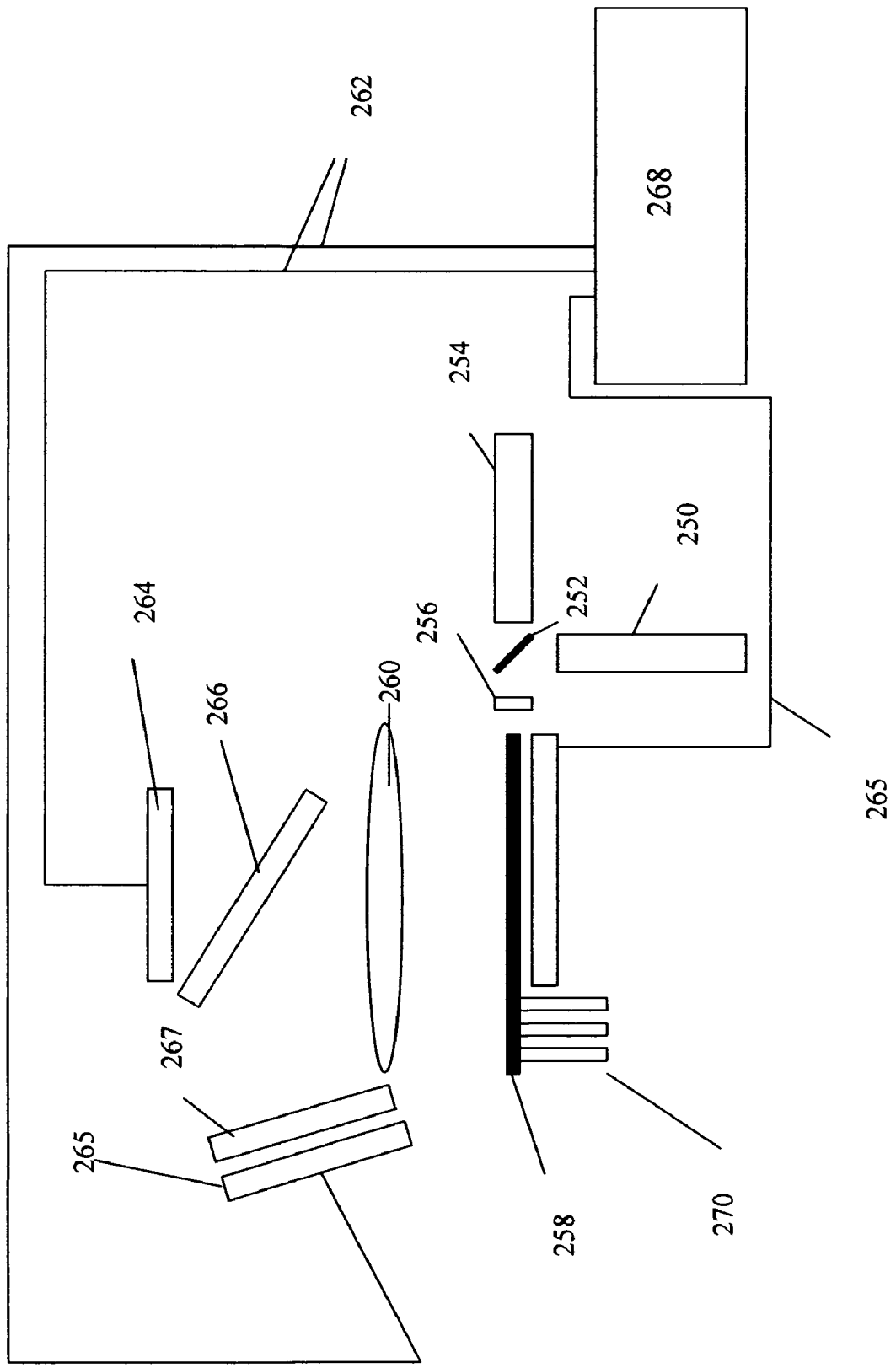
FIG. 4 is a simplified diagrammatic view of the MEMS particle sorting system.

The details of the optical system are shown in FIG. 4. Two lasers may be used to allow the flexibility to induce fluorescence in multiple markers: i.e. a first $Ar^+$ laser operating at 488 nm, and the second a Rhodamine 6-G dye laser operating at 590 nm. The beams may be combined with a beamsplitter/turning mirror 252, and focused into a line on the optically transparent layer 88 by a cylindrical lens 256. The two dimensional sheet of light propagates within the optically transparent layer 88. Fluorescent light emanating from above the parallel channels 108 (if an appropriate fluorescing cell is present) passes out of the MEMS chip through optical cover 81 and the collection lens 260 directs an image of the chip surface onto the set of light detectors 264 and 265, through the set of filters 266 and 267. The light detectors 264 and 265 may be charge coupled device (CCD) cameras or photomultiplier (PMT) tubes, for example. The filters are used to select only the desired fluorescence signal of the marker. In the case of sorting HSCs in which both CD34 and Thy-1 antigens are used, the filters are selected to pass only the wavelengths for the tags for those antigens, respectively. In general, then, the camera detectors are in the dark except during the rare events of detection of a fluorescence signal. The detection of fluorescence by the light detector (or the simultaneous detection of both signals, one in each camera) indicates the presence of a human hematopoietic stem cell in the sample manifold, at the position in the array indicated by the light detector. The electronics then causes the appropriate actuator to be energized, diverting the sample cell into the appropriate manifold. The actuator is then positioned back to its initial state.

In the implementation described herein, the fluorescent light passing through collection lens 260 impinges first on one filter, filter 266. Light of the proper wavelength passes through filter 266 into the first high speed detector 264. All other light reflects from the surface of filter 266, and impinges on filter 267. Light of the proper wavelength for that filter passes through into the second high speed detector 265. In this way, efficient use is made of the available light to optimize signal-to-noise and speed in the system.

A variety of state-of-the-art camera systems are available to serve as the high-speed light detectors. For example, Photron USA (San Diego, Calif.) markets the PhotoCAM 250 CL, a monochrome camera with 10,000 frames per second performance, adequate for the speed requirement, with over 4000 pixels in each frame, sufficient for this application. Alternatively, as mentioned above, a photomultiplier tube (PMT) may also be used as the light detector. If additional sensitivity is required for a particular application, an intensifier plate may be added in front of the camera's detector. These are common in industry, known as microchannel plates (MCP), and are an array of channeltrons.

In practice, filters 266 and 267 may not be individual filters, but filters on respective filter wheels, so that one particular filter may be selected simply by rotating the wheel. In this way, the machine can easily be configured to detect different wavelengths.

General-purpose computer 268 may direct the operation of the various electronics units through a multi-pin connector 265 to control the actuators, and harness 262 to acquire the signal from each light detector. The general purpose computer 268 also controls laser pulse timing, if a pulsed laser is used. The blood is delivered to the chip and the waste and sorted cells are taken away from the chip through the set of plumbing tubes, 270, typically made of polyimide-jacketed quartz or a polymer material such as polyetheretherketone (PEEK), and glued into the MEMS chip.

Figure 5:
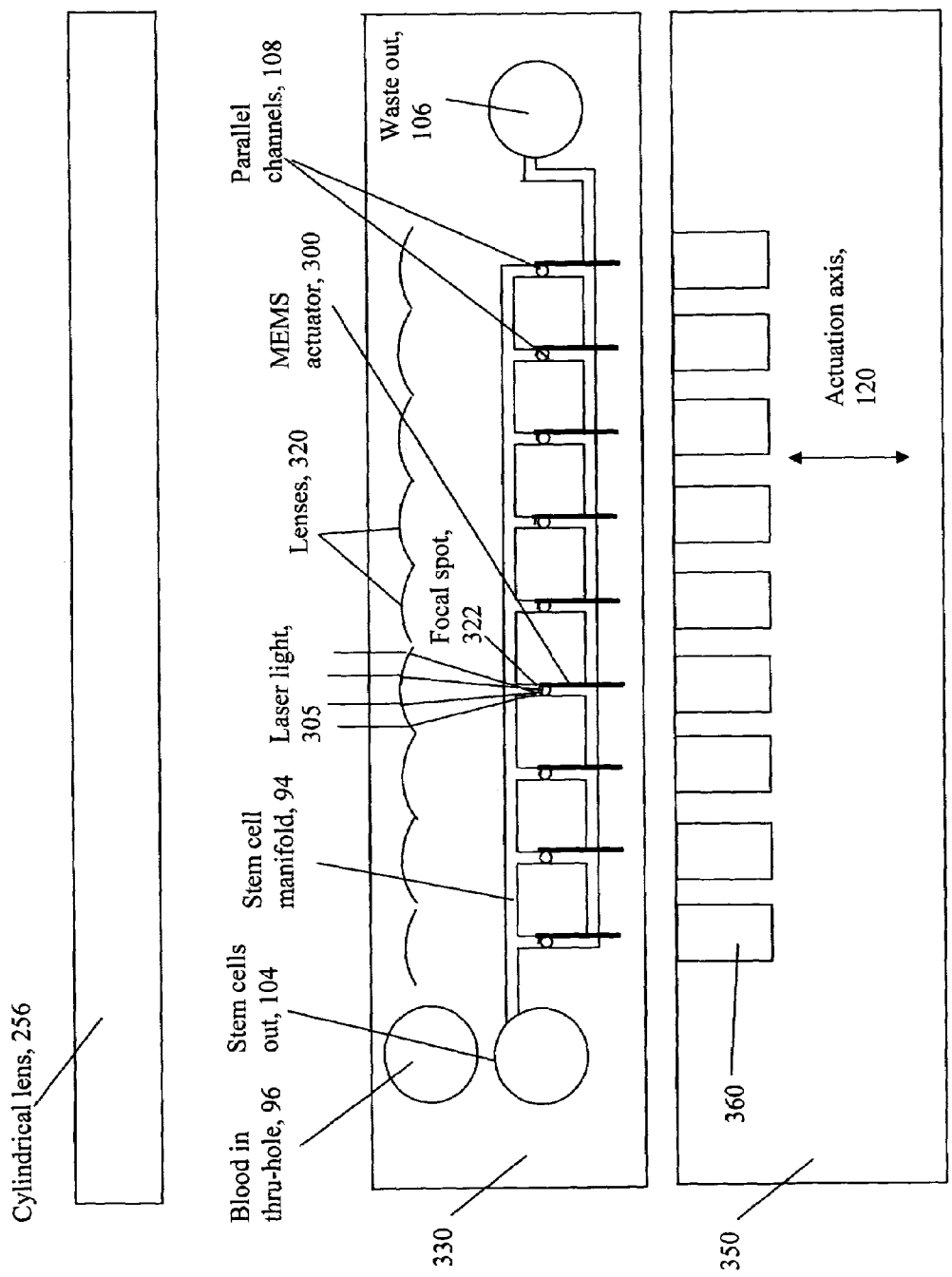
FIG. 5 is a diagrammatic view of a one-dimensional MEMS particle sorting system, showing the two-piece actuator.

As was mentioned above, the n×m array of parallel channels and actuators may also be a one-dimensional 1×32 array, for example, of parallel channels and actuators as shown in FIG. 5. FIG. 5 shows a MEMS particle sorting apparatus 330, including an optical layer, actuator layer and manifold layer in plan view. The microactuator body portions 300 on MEMS particle sorting apparatus 330 may be of the extensible/retractable type, rather than the pivoting type 192 as was shown in FIG. 3, and may move along the actuation axis 120 shown in FIG. 5. There may be several advantages of the arrangement shown in FIG. 5. For example, the extensible/retractable actuator may be simpler to build, and may also have the actuator formed in two pieces, a microactuator body portion 300 formed on MEMS chip 330 and a force-generating part 360 formed separately as a force-generating portion 350. Using this approach, each of the microactuator body portion 300 and the force-generating part 360 may be fabricated using different tools, with each optimized independently.

In addition, the one-dimensional MEMS particle sorting apparatus 330 also allows the laser light to be brought from a line focus to a focus at a plurality of single points, which may have advantages in terms of the timing of the movement of the microactuator body portion 300. Additional details of the structures and method of fabrication of the optical elements used to focus the laser light may be found in co-pending U.S. patent application Ser. No. 11/196,291, filed on an even date herewith and incorporated by reference in its entirety.

In particular, the laser light 305 depicted in FIG. 5 may enter the one-dimensional MEMS particle sorting chip 330 in substantially a single plane, and pass through one of a set of lenses 320. Lenses 320 may be refractive lenses, and may focus sections the laser light 305 down to, for example, a single spot at a well-defined point 322 prior to the opening of the parallel channel 108. The detection of fluorescence by the photodetectors 264 and 265 then indicates that a target cell, for example, a human hematopoietic stem cell, is in a well-defined location relative to the microactuator body portion 300. The detection of the fluorescence event may then set the timing sequence of the subsequent microactuator body portion 300 movement with greater precision, thereby improving the accuracy of the cell sort and the purity of the sorted sample. It should be appreciated that the lenses 320 may be formed integrally with the particle sorting chip, using a transmissive material, with, for example, a higher index of refraction than air. As one exemplary embodiment, lenses 320 may be formed of a transmissive photoresist such as SU8. SU-8 is a high contrast, epoxy-based photoresist developed by IBM of Armonk, N.Y. The index of refraction of SU-8 is 1.5-1.7 from about 380 nm to about 750 nm, and SU-8 may be virtually transparent over this range. Alternatively, the optically transparent material may be any optically transparent material such as quartz, silica, alumina, indium-tin-oxide or glass, which may be formed to have at least one optically reflective and/or optically refractive surface.

FIG. 6a is a schematic illustration showing further detail of the microactuator body portion 300 and force-generating portion 360 of the actuator. The microactuator body portion 300 may be extensible/retractable along the axis 316 by interaction with an electromagnetic motor which may be the force-generating portion 360. The force-generating portion may include at least one magnetizable driving core, wound with a coil of wire. In the illustrated embodiment, there are a pair of magnetizable driving cores 362 and 364, around which a pair of coils 363 and 365 are wound. When current flows in the coils 363 and 365, a magnetic field M is generated inside driving cores 362 and 364, in the direction shown in FIG. 6a. The magnetic flux circulates within the flux guiding driving cores 362 and 364, and across the small gap, g, between the microactuator body portion 300 and the force-generating portion 360. The flux then circulates through motor poles 304 and 306, by flowing across the gap 305. At the location of the gap 305, the flux extends into the surrounding region and interacts with a magnetizable portion 302 which is affixed to the rigid body 308 of the actuator. A flux return path is provided by rear magnetizable portion 366, which may lie across the back face of magnetizable cores 362 and 364. The interaction of magnetizable portion 302 with the flux in the gap 305 draws the magnetizable portion 302 into the gap 305, and therefore draws a diverter 310 affixed to the actuator rigid body 308 to a position beneath the parallel channel 108. This changes the direction of flow out of the parallel channel 108 from that shown in FIG. 6a to that shown in FIG. 6b.

FIG. 6a shows the microactuator body portion 300 in the default position, wherein the diverter 310 of the microactuator body portion 300 directs the fluid stream into the waste/return manifold 312. In FIG. 6b, the magnetizable portion 302 is interacting with the gap 305 between the motor poles 304 and 306, and therefore has been retracted into the gap 305. This retraction pulls the diverter 310 to a position in which it is below the parallel channel 108, and therefore directs the fluid stream into the sort/save manifold 314. Although not depicted in FIGS. 6a and 6b, the microactuator body portion 300 may also include a set of restoring springs (not shown in FIGS. 6a and 6b), which return the magnetizable portion 302 and rigid body 308 from their actuated position shown in FIG. 6b to their default position shown in FIG. 6a.

Figure 7B:
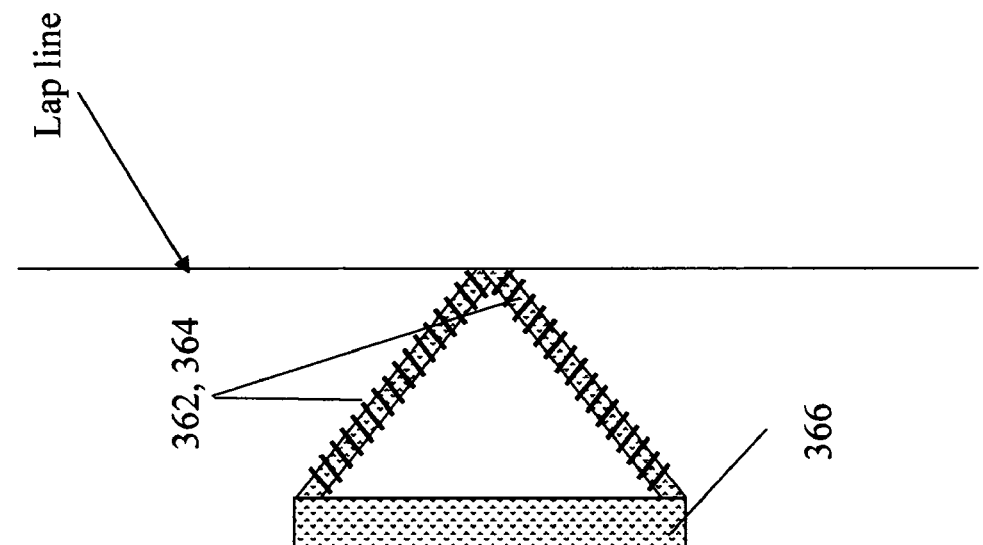
FIG. 7b shows the force-generating portion of the two-piece actuator after lapping.
Figure 7A:
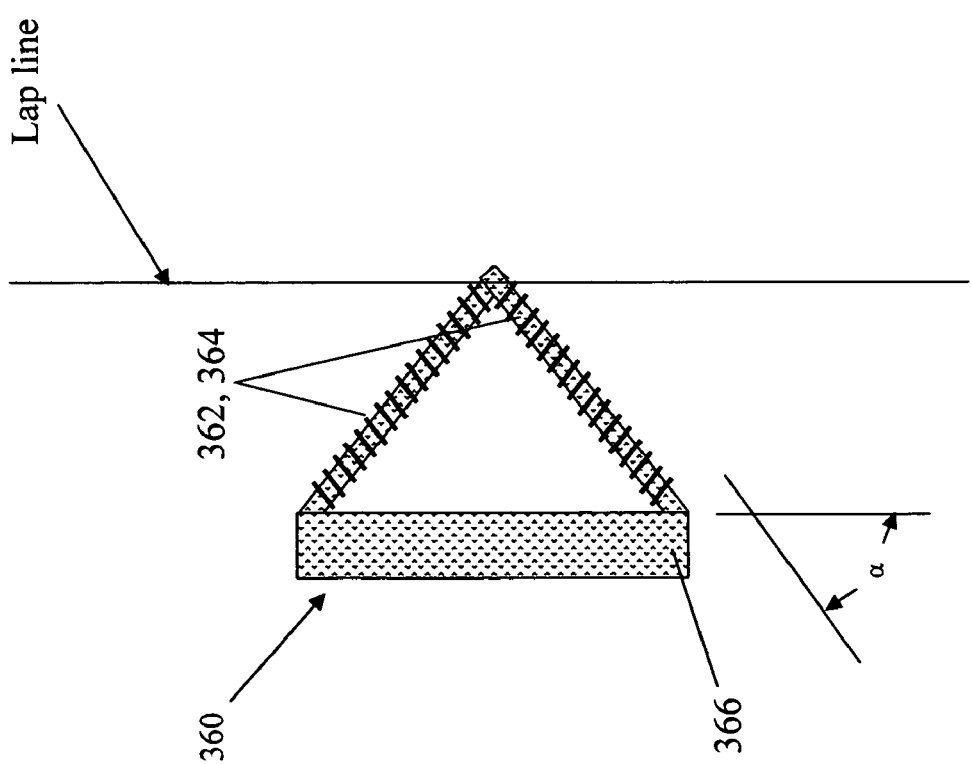
FIG. 7a shows the force-generating portion of the two-piece actuator before lapping.

FIGS. 7a and 7b are side views of the force-generating portion 360 of the micromechanical actuator. In order to reduce the pitch between adjacent actuators, and therefore to increase the number of devices on a given wafer area and reduce cost, the motor poles 304 and 306 may need to be placed as close together as possible. As a result, the driving coils 363 and 365 and driving cores 362 and 364 may also need to be as close together as possible. In order to enhance manufacturability of the closely spaced coils 362 and 364, they may be wound on legs which are splayed as shown in FIGS. 7a and 7b. The angle α between the splayed legs may be any convenient angle, for example from 45 degrees to 70 degrees which allows easy fabrication, and may preferably be around 60 degrees.

Figure 8:
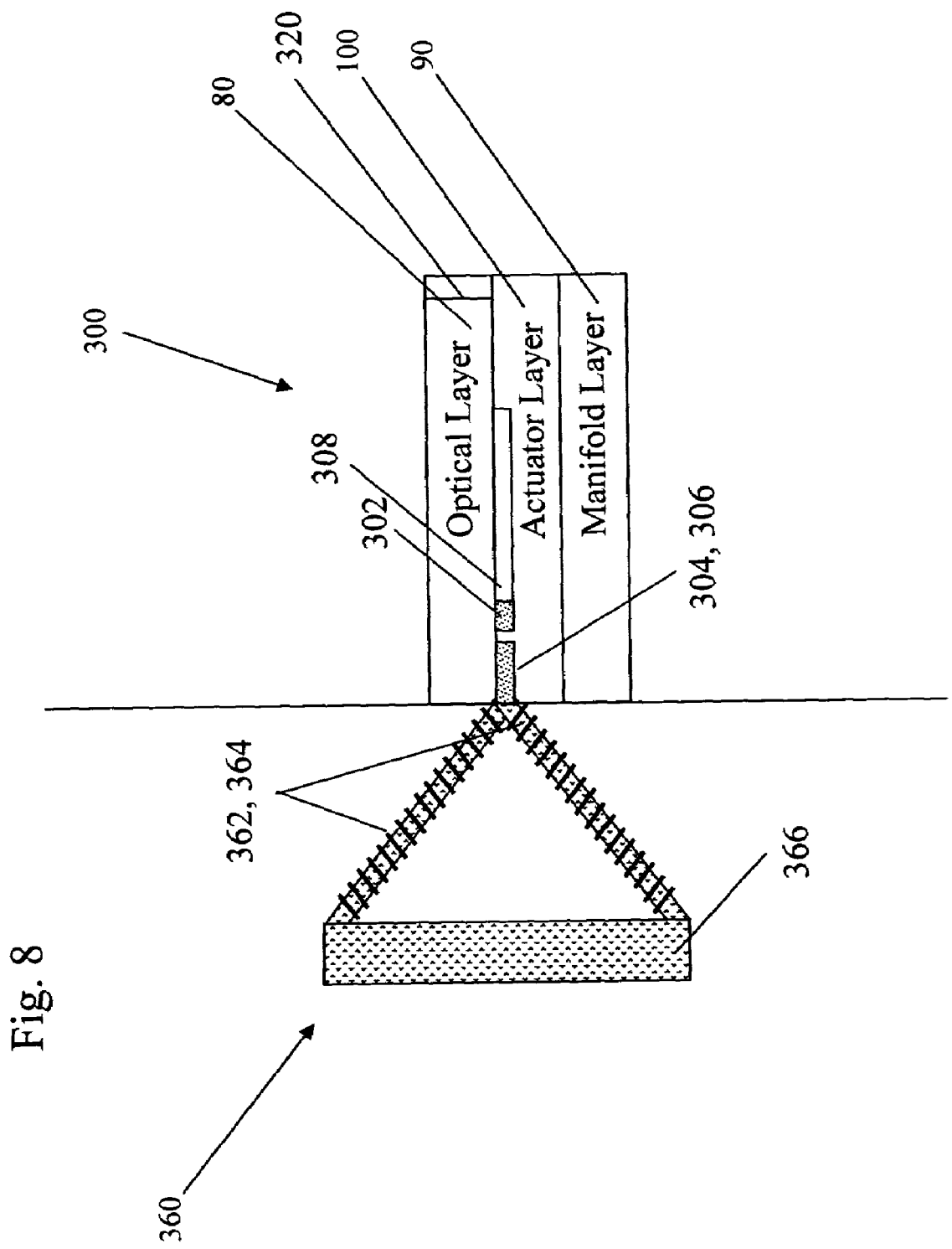
FIG. 8 illustrates the alignment of the force-generating portion of the two-piece actuator with the MEMS cell sorting chip.

The force exerted on the microactuator body portion 300, and therefore the acceleration and speed of the actuator rigid body 308, depends on the amount of flux coupled between the driving cores 362 and 364, and the motor poles 304 and 306. In order to increase the flux-coupling capability of the microactuator body portion 300, the motor poles 304 and 306 may be made of high permeability material, such as 45/55 nickel-iron permalloy. The coupling efficiency between the driving cores 362 and 364 and the motor poles 304 and 306 depends, in turn, on the magnitude of the gap, g, between them as shown in FIG. 6a. To reduce this gap to as small a value as possible, the splayed legs shown in FIG. 7a are lapped back to a lapping line shown in FIGS. 7a and 7b. The shape of the lapped driving cores 362 and 364 is shown in FIG. 7b. The lapping process thus allows the faces of the driving cores 362 and 364 to abut the faces of the motor poles 304 and 306, in order to enhance the coupling of the magnetic flux from the driving cores 362 and 364 to the motor poles 304 and 306. FIG. 8 shows the disposition of magnetic driving cores 362 and 364, relative to the motor poles 304 and 306, and magnetizable portion 302 coupled to rigid body 308. As shown in FIG. 8, the motor poles 304 and 306, the magnetizable portion 302 and rigid body 308 are all contained in the actuator layer 100 of the MEMS particle sorter chip, whereas the refractive lens 320 is contained in the optical layer 80. As shown in FIG. 8, the driving cores 362 and 364 are brought to a position directly adjacent to and in the same plane as the motor poles 304 and 306, and to as close a proximity as the flatness of the surfaces allows. The lapping may be achieved using techniques commonly known in the art, such as placing the force-generating portion 360 against a rotating lapping wheel, to achieve a flatness of about 1 µm across the magnetic driving cores 362 and 364.

As mentioned above, the force exerted on the microactuator body portion 300, and therefore the speed of the device, depends on the amount of flux generated by the force-generating portion 360 of the micromechanical actuator. In order to increase the amount of flux, the coils 363 and 365 may be wound tightly and designed to carry a relatively large amount of current. In order to handle the heat generated by operation of coils 363 and 365, the coils may be potted in a thermal compound, which carries heat from the coils 363 and 365 to the driving cores 362 and 364 and then to the flux return rear portion 366.

The driving cores 362 and 364 and flux return rear magnetizable portion 366 may be fabricated using standard macroscopic-scale machining tools from common high saturation, soft magnetic materials such as pure iron or iron-cobalt alloys, and the coils 363 and 365 wound on the driving cores 362 and 364 by machine or by hand. The coils 363 and 365 may be wound with about 50 turns on each leg capable of 25 ampere turns of magnetomotive force (MMF), and the legs may be disposed with a 500 micrometer pitch. The coils are capable of magnetically saturating magnetizable cores 362 and 364 of cross section of about 150×500 µm and 4 millimeter length.

Figure 9:
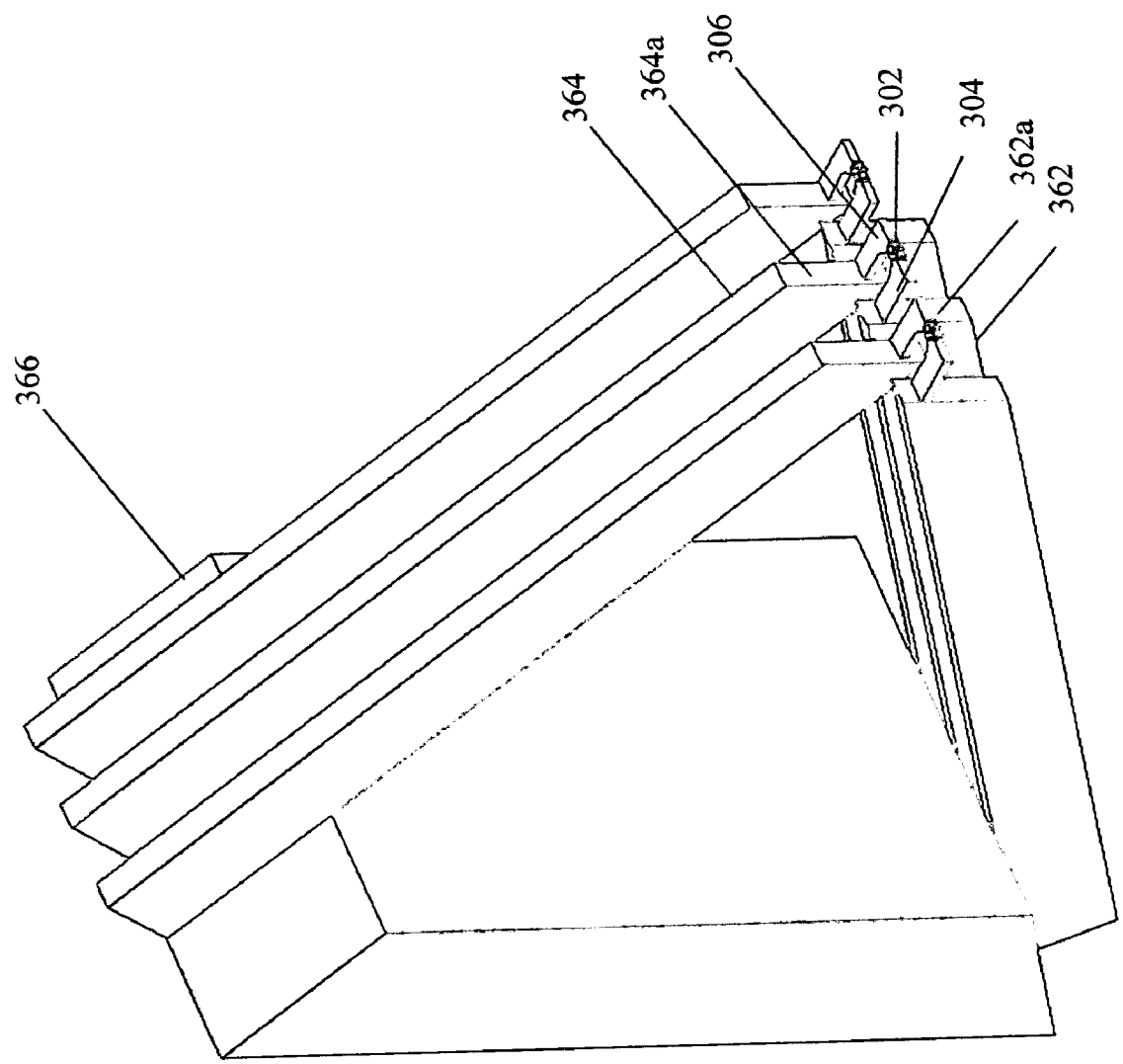
FIG. 9 is an isometric view of the force-generating portion in communication with the stationary poles of the MEMS particle sorting device.

FIG. 9 shows an isometric view of the force-generating portion 360 disposed in a workable arrangement with respect to the motor poles 304 and 306. For clarity, the coils 363 and 365 and the remainder of the actuator layer 100 are not shown in FIG. 9. Only the motor poles 304 and 306 and magnetizable portion 302 of the actuator layer 100 are shown in FIG. 9. The lapped surface 362a of driving core 362 is brought very close to, within about 1 µm, of motor pole 304. With the parts oriented flat against each other, the lapped face 364a of driving core 364 is brought very close to, or touching, motor pole 306. Because of the very close proximity of motor poles 304 to driving cores 362, flux generated in driving cores 362 jumps across the 1 µm gap and circulates through motor pole 304 and across the gap 305 through the magnetizable portion 302 which is affixed to the rigid body 308 (refer to FIG. 6a). From magnetizable portion 302, the flux jumps again across the narrow gap 305 to motor pole 306, and then back across the lapped gap to driving core 364. The magnetic circuit is completed by the rear magnetizable portion 366.

Figure 10:
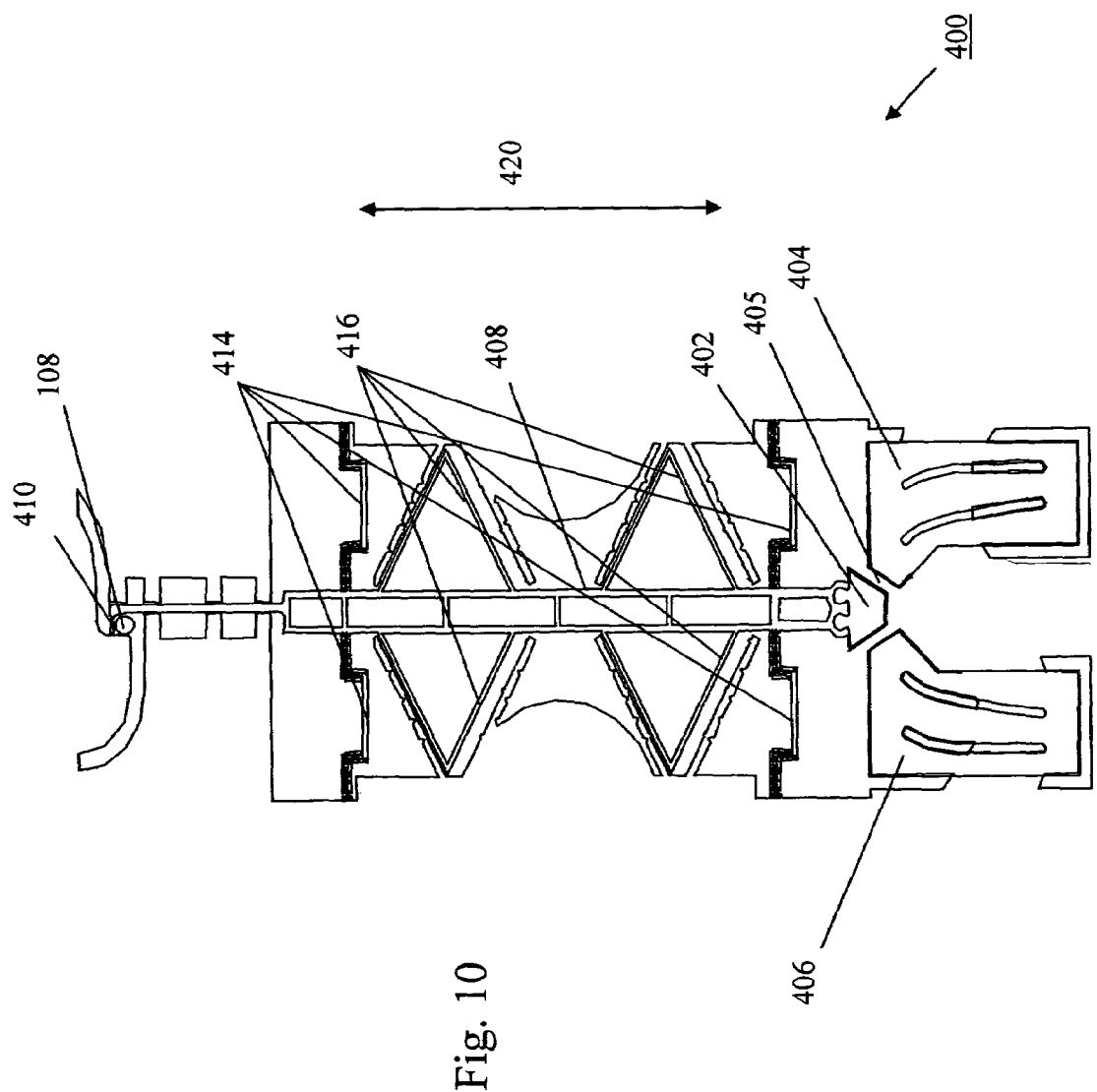
FIG. 10 shows a first exemplary embodiment of the actuator body portion of a two-piece actuator.

FIG. 10 shows a first exemplary embodiment 400 of actuator body portion 300 useable in the arrangement shown in FIGS. 6a and 6b. Actuator portion 400 includes a diverter 410, a rigid body 408, a magnetizable portion 402, and motor poles 404 and 406. Actuator portion 400 may also include a set of restoring springs 414 which exert a restoring force on actuator rigid body 408 to return it to its original extended (default) position from its actuated retracted position. The restoring springs may include four 90 degree bends, which allow the spring to flex in the direction 420 shown in FIG. 10. The actuator portion 400 may also include a set of damping plates 416, which are flat plates separated by a narrow gap.

Figure 11:
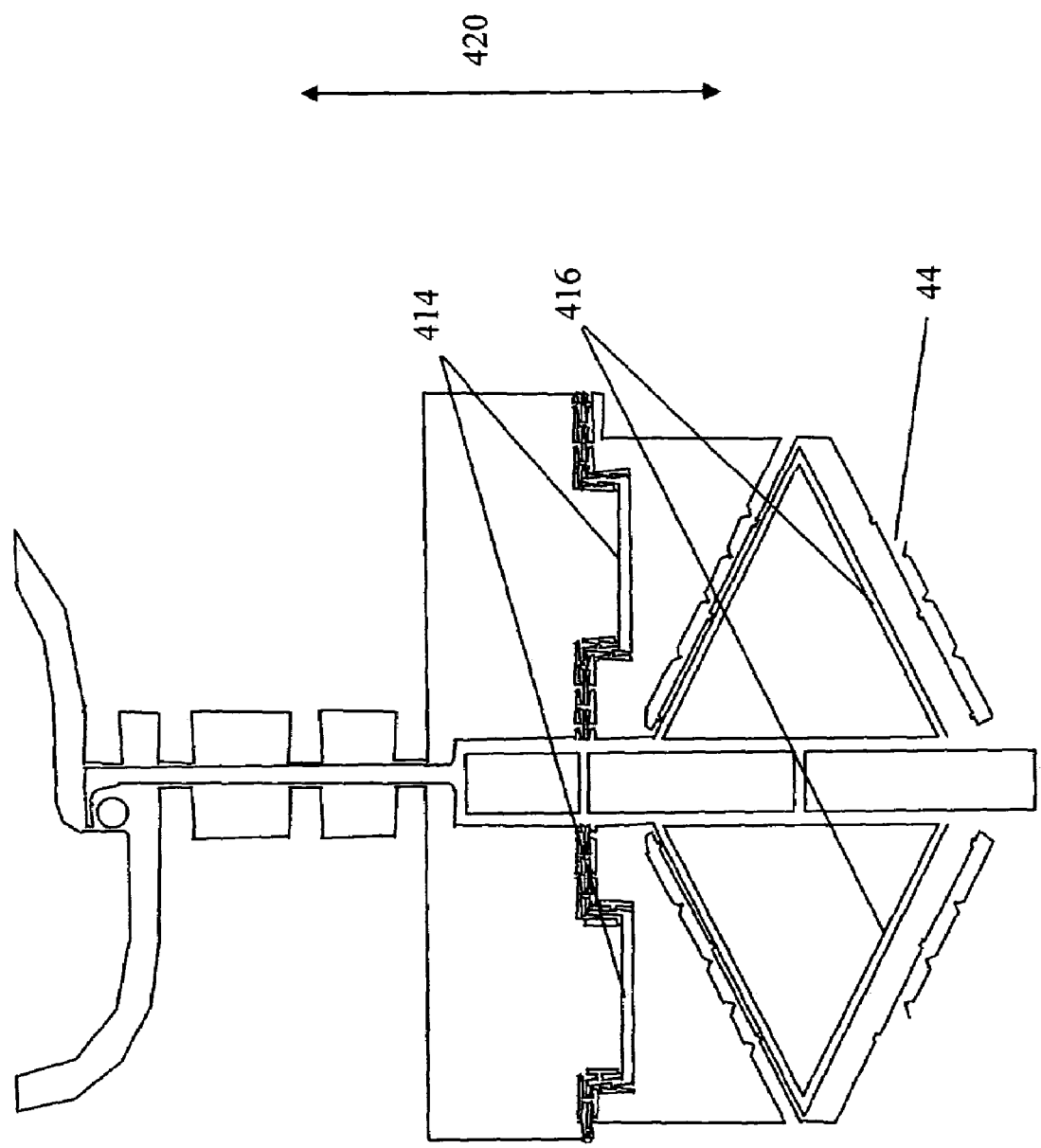
FIG. 11 shows greater detail of the features of the first exemplary embodiment of actuator body portion of FIG. 10.

The restoring springs 414 and damping plates 416 are shown in greater detail in FIG. 11. As shown in FIG. 11, the restoring springs 414 may each include four 90 degree bends, which allow the spring to flex in the direction 420 shown in FIG. 11. Using the design shown in FIG. 11, the restoring springs may be non-linear, such that the spring constant k increases with increasing deflection. This may be a convenient attribute, as the actuation force may also increase as the magnetizable portion 402 is drawn into the gap 405 between the stationary plates. Therefore, full use may be made of the additional motor force as the magnetizable portion 402 is drawn towards the motor poles 404 and 406, allowing more energy to be stored in the springs for a quicker return time.

The damping plates 416 may resist residual oscillation by drawing viscous air into the gaps created by the increasing the distance between the plates, as the actuator is drawn toward the gap 405. This is known as squeeze-film damping, and is well known in the art. An exemplary spacing between the damping plates may be 2 µm, for multiple damping plates about 300 µm in length and about 50 µm in thickness. However, other dimensions may be used, depending on the application. As shown in FIG. 10, as the rigid body 408 is drawn down by the interaction of the magnetizable portion 402 with the gap 405 between the motor poles 404 and 406, the separation of the upper plates increases, creating a vacuum which draws air into the region. Simulataneously, the separation of the lower plates decreases, forcing air out of the region. The viscosity of the air may create drag on the plate motion, thereby damping residual oscillation.

The gap 405 between the magnetizable portion 402 and the motor poles 404 and 406 may be lithogaphically defined, and may be, for example, about 25 µm in the extended position. Therefore, the total throw of the actuator portion 400 may be about 25 µm. The shape of the magnetizable portion 402 in the embodiment shown in FIG. 10 may follow the contour of the gap 405 formed between the motor poles 404 and 406. For this reason, the gap between the magnetizable portion 402 and motor poles 404 and 406 may be relatively uniform, thereby enhancing the efficiency of the flux coupling from the motor poles 404 and 406 to the magnetizable portion 402. This may, in turn, enhance the force generated by the actuator portion 400 in response to the driving cores 362 and 364. However, the first embodiment 400 of microactuator body portion 300 may be susceptible to stiction forces arising from contaminants, and particularly from meniscus forces arising from the liquids used in the processing to form the features 402, 404 and 406.

Figure 12:
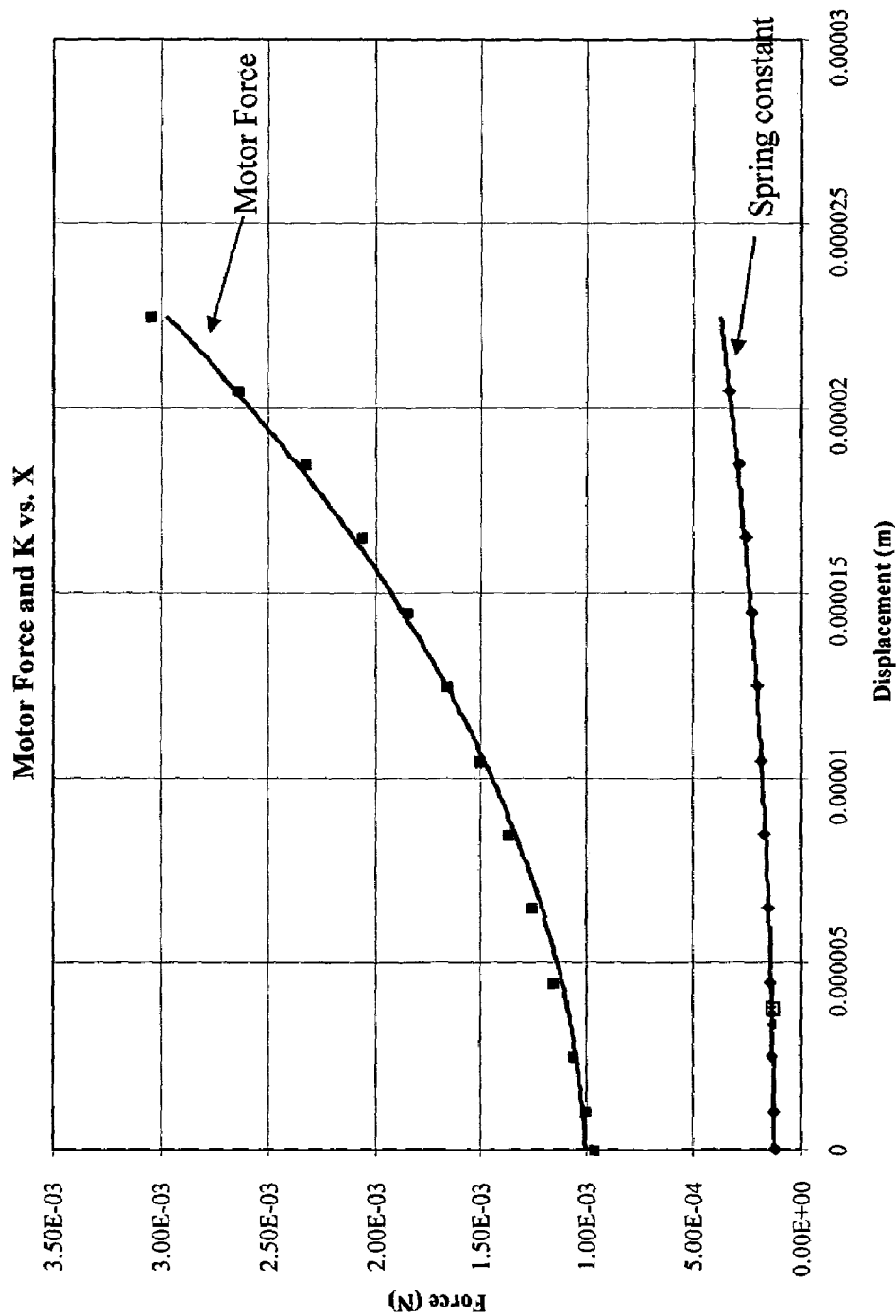
FIG. 12 is a force-versus-displacement diagram for the actuator body portion of FIG. 10 and the force-generating portion of FIG. 8.

FIG. 12 is a plot of the calculated values of the actuation force and spring constant versus displacement of the magnetizable portion 402. As shown in FIG. 12, the actuation force increases from about $10^{-3}$ Newtons to about $3 \times 10^{-3}$ Newtons as the magnetizable portion 402 is drawn from its default position at 0 µm displacement to its fully retracted position at about 23 µm displacement. Because of the above-described design of the restoring springs 414, the spring constant also increases over this range. As a result, the rigid body 408 may be smoothly retracted by the combination of the interaction of the magnetizable portion 402 with the gap 405, and the restoring springs 414.

Figure 13:
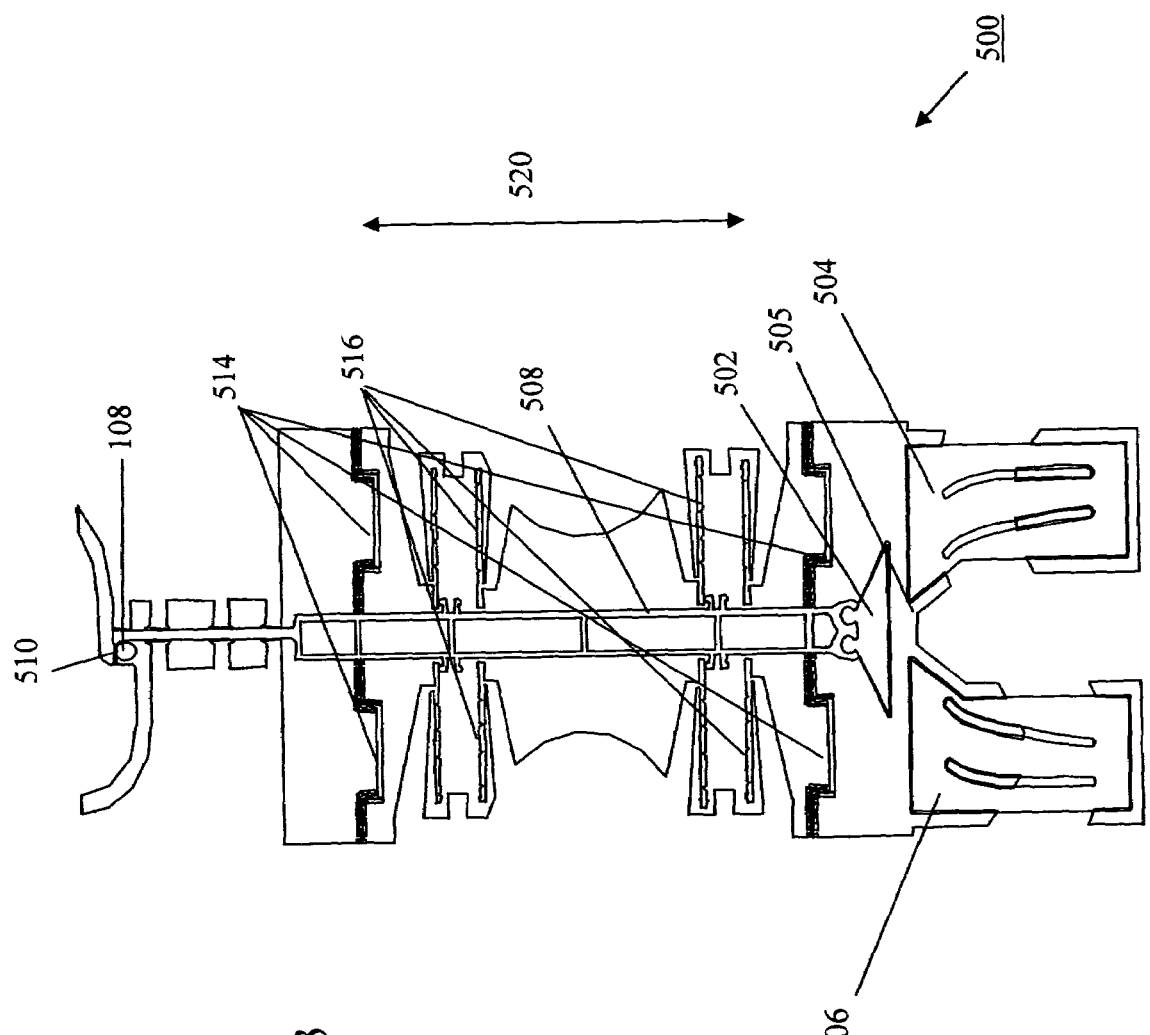
FIG. 13 shows a second exemplary embodiment of the body portion of a two-piece actuator.
Figure 14:
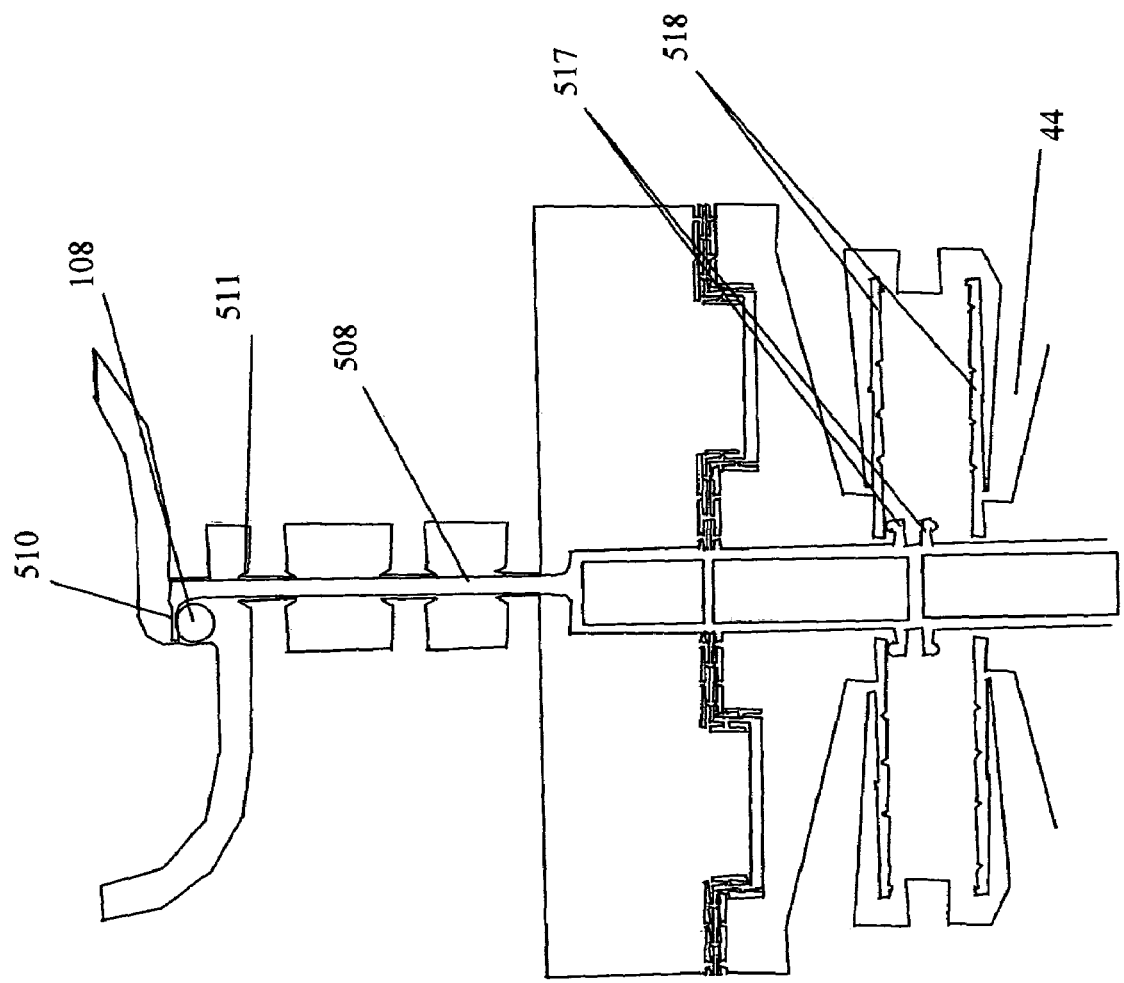
FIG. 14 shows greater detail of features of the second exemplary embodiment of the body portion of the two-piece actuatot.

FIG. 13 shows a second exemplary embodiment 500 of microactuator body portion 300, useable in the configuration shown in FIGS. 6a and 6b. Like the first exemplary embodiment 400 shown in FIG. 11, microactuator 500 includes four restoring springs 514, each with four 90 degree bends which provide a restoring response similar to that illustrated in FIG. 12. However, the damping plates 416 of the first exemplary embodiment are replaced by crash stops 516 which limit the travel of the rigid body 508. The design of the crash stops is shown in greater detail in FIG. 14. The crash stops include a protrusion 517 rigidly affixed to the rigid body 508, and crash stop plates 518 integrally formed with the silicon substrate 44. The magnetizable portion 502 of microactuator 500 is also of a different design compared to magnetizable portion 402 of actuator portion 400. As the magnetizable portion 502 interacts with motor poles 504 and 506, it is drawn nearer to gap 505, which lowers the rigid body 508 along with protrusion 517 until it contacts the crash stop plate 518. The crash stops 518 may prevent further travel of the rigid body 508 along direction 520, and therefore limit the throw of microactuator 500. The crash stop plates 518 may also have small notches or bumps patterned on their faces at appropriate spacings. This may cause the energy imparted to the stop plates from the impact of the actuator to be rapidly dissipated in higher frequency modes, rather than remaining at the primary resonant frequency of the crash stop plates 518. The result may be a more rapid damping of the motion of the crash stop plates 518 themselves.

In another embodiment, the travel of rigid body 408 or 508 may be limited by providing a time-varying pulse to force-generating portion 360, which then produces a time-varying force which may essentially brake the motion of the rigid body 408 or 508.

It has also been observed that contact between magnetizable nickel-iron (NiFe) permalloy forms a highly damped contact interface. Because such damping is effective in reducing residual motion such as bouncing against the crash stop 518, a NiFe/NiFe interface may also be provided as crash stop material. This may be achieved by, for example, lowering the lower crash stop 518 or raising the protrusion 517 so that the range of motion is limited by the interference of the magnetizable portion 502 with the motor poles 504 and 506, rather than with interaction of the rigid silicon body 508 with the rigid silicon crash stop 518. Magnetizable portion 502 and motor poles 504 and 506 may all be formed from NiFe permalloy, providing a permalloy crash stop material interface. Such an advantageous NiFe interface may also be provided on the other end of travel of the rigid body 508, by, for example, providing a crash stop which is coupled to the stationary NiFe magnetizable motor poles 504 and 506.

Microactuator 500 also has a different shape for the magnetizable portion 502 of rigid body 508. The magnetizable portion 502 is shaped with a flat bottom instead of the shaped contour of magnetizable portion 402 of microactuator 400. The flat bottom shape of magnetizable portion may be less sensitive to stiction and therefore easier to fabricate. However, the flux coupling between magnetizable portion 502 and the motor poles 504 and 506 may be less effective and therefore provide less force to the microactuator 500, compared to microactuator 400. As a result, microactuator 500 may not move as quickly as microactuator 400.

However, embodiment 500 may have other advantages relative to embodiment 400. For example, embodiment 500 may be less susceptible to lateral pull-in of the motor, in which if magnetizable portion 402 is slightly offset from the midline between motor poles 404 and 406, the force emating from the closer motor pole 404 or 406 is larger than the force emanating from the more-distant motor pole. This unbalanced force causes the magnetizable portion 402 to be pulled laterally, and as the magnetizable portion 402 is pulled further to the side, the lateral force increases further. In contrast, embodiment 500 is relatively insensitive to this effect.

Figure 15:
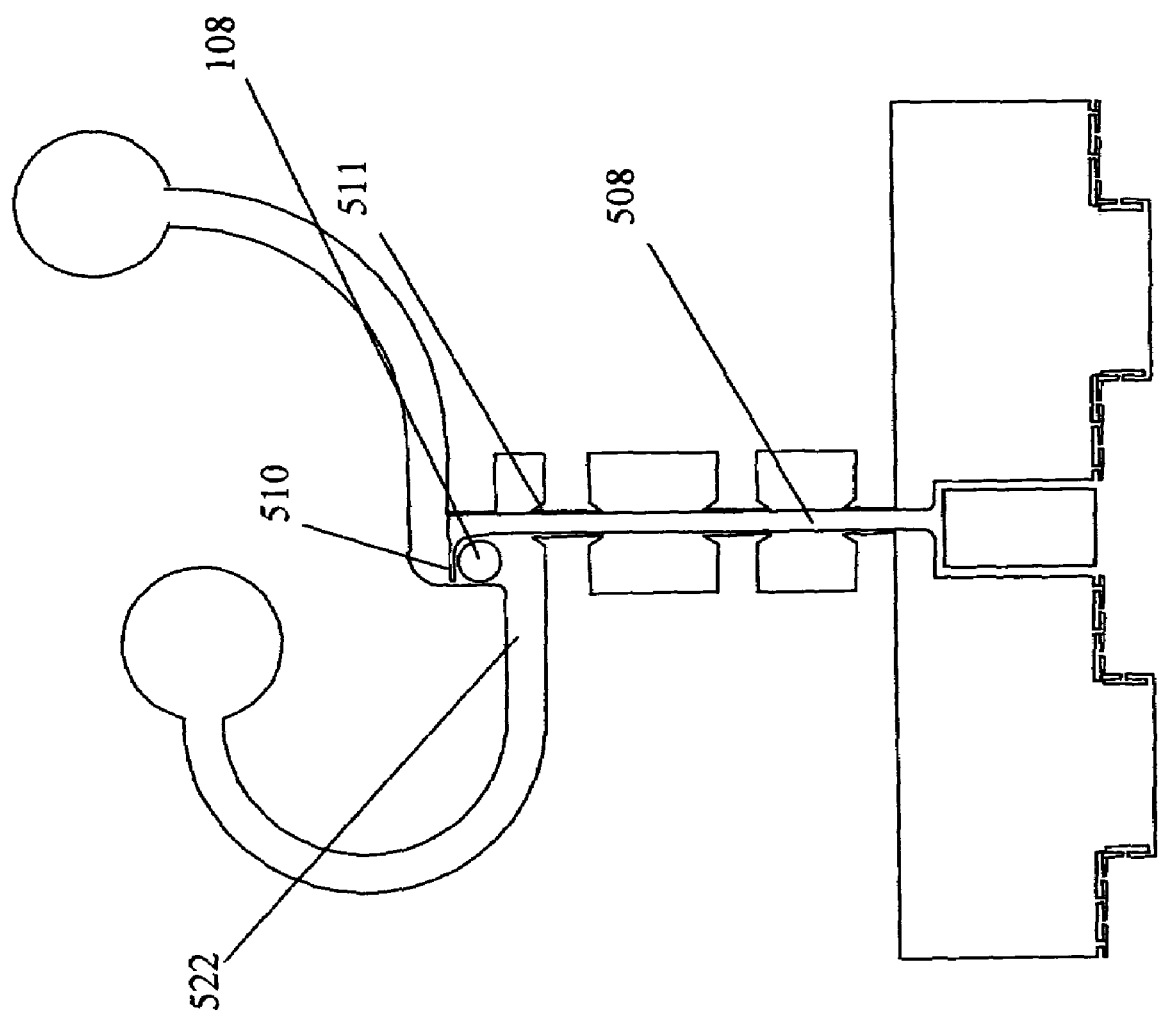
FIG. 15 shows yet further detail of the second exemplary embodiment of the body portion of the two-piece actuator of FIG. 13 with the actuator in the waste/return position.

FIG. 15 shows additional detail of the top portion of the second exemplary embodiment 500 of the microactuator body portion 300. The top portion is shown in the extended (default) position, wherein the diverter 510 is disposed above the parallel channel 108, thereby directing fluid from the parallel channel 108 into the lower channel 522, which is coupled to a waste/return reservoir.

As shown in FIGS. 10 and 13, embodiments 400 and 500 may have diverters 410 and 510 which are directly attached to the magnetizable portions 402 and 502 by rigid bodies 408 and 508. However, it should be understood that the diverters 410 and 510 may also be attached to the magnetizable portions 402 and 502 by one or more flexible hinges and/or springs, in order to provide mechanical advantage. The mechanical advantage provided by the hinges and/or springs may increase the throw of actuators 400 and 500, while maintaining a rapid actuation time as determined by the design of actuators 400 and 500.

Figure 16:
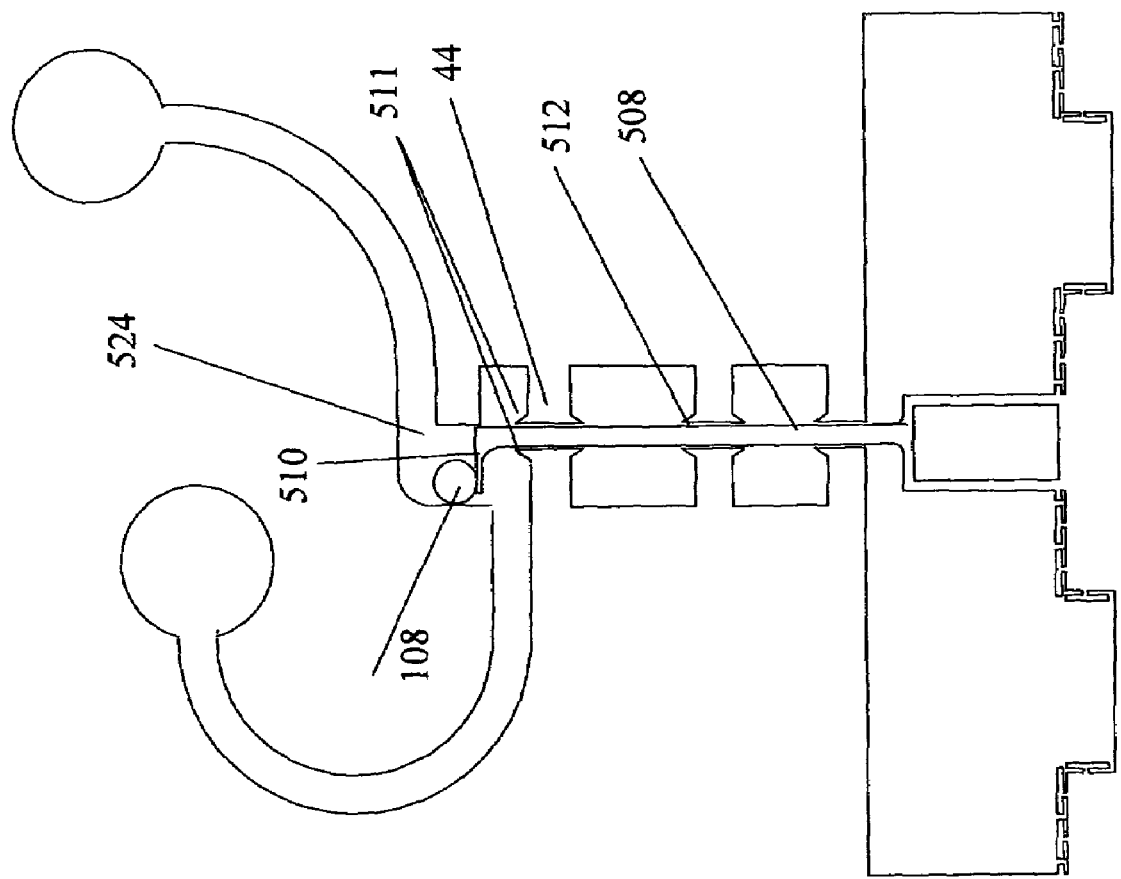
FIG. 16 shows yet further detail of the second exemplary embodiment of the body portion of the two-piece actuator of FIG. 13 with the actuator in the sort/save position.

FIG. 16 shows additional detail of the second exemplary embodiment 500 of the microactuator body portion 300 in the retracted position illustrated in FIG. 6b. In this position, the magnetizable portion 502 is drawn toward the gap 505, retracting the magnetizable portion affixed to the rigid body 508. This action withdraws the diverter 510 to a position beneath the parallel channel 108. As a result, fluid exiting the parallel channel 108 is directed into the upper channel 524, which is coupled to a sort/save reservoir (not shown). Therefore, upon detection of fluorescence emanating from a component of interest, the driving coils are energized, drawing the rigid body into the retracted position and directing the fluid stream into the sort/save channel 524. The particle of interest are thereby separated from the fluid stream and stored for later collection. Although not shown in FIG. 16, it should be understood that the restoring springs, 514, will in general also be deflected by the retraction of the rigid body 508.

As shown in FIG. 16, the rigid body 508 may be separated from the substrate 44 by a very narrow channel 512. The shape of this channel may be formed as shown in FIG. 16, in order to promote the formation of a fluidic seal between the fluid containing channels 522 and 524, and the air-containing regions around the lower portion of the rigid body 508. In particular, since the gaps between the substrate 44 and the rigid body 508 are of the order 1 μm, fluid is free to flow from the parallel channel 108 to the recesses of the microactuator 500 and out of the microactuator body portion 300. Allowing fluid to flow into the otherwise dry regions of microactuator 500 and 400 would also reduce the actuation time for the devices, as the drag of the fluid may substantially slow the actuation motion of the device. Therefore, a fluidic seal needs to be formed between the fluid portion near parallel channel 108, waste/return channel 522 and sort/save channel 524, and the rest of the microactuator 500. To form this fluidic seal, the actuator portion may be dipped in a fluorocarbon lubricant, such as AM2001 or Z-dol, common lubricants sold by Dupont Corp. (Wilmington, Del.). The resulting fluorocarbon film may be approximately 10 to 20 Angstroms thick, and with some bonding affinity for the wafer surface. Alternatively, in order to avoid having the lubricant interfere with the bond line between the actuator layer and the optical layer, the lubricant may be vapor deposited, after bonding of the actuator layer 100 to the optical layer. The function of the fluorocarbon film is to reduce wetting of the wafer surfaces.

While the fluid mixture may be driven by pressure through parallel channels 108, past the microactuator 400 or 500 and into one of the channels 522 or 524, the fluid mixture may not wet or flow easily past the region defined by the set of protrusions 511 forming the channel 512, because of the formation of a meniscus bounding the fluid region. In order to enhance the meniscus integrity between the fluid mixture and the substrate wall, the protrusions 511 may be shaped as shown in FIG. 16. The radius of curvature of the portion of the protrusion 511 extending into the fluid region may be very small, forming a relatively firm meniscus between the substrate wall protrusion 511 and the fluid region.

Figure 17:
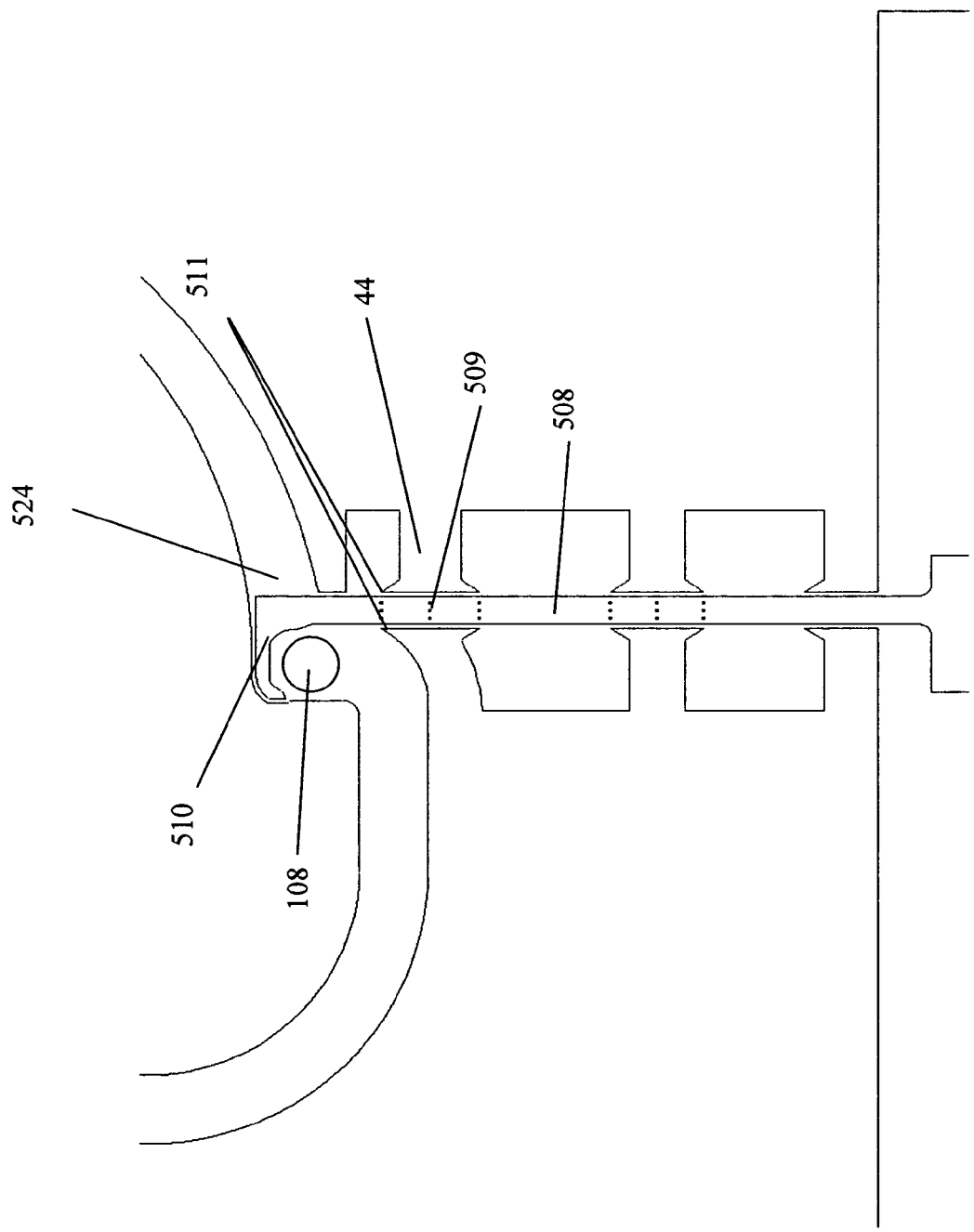
FIG. 17 shows yet further detail of the second exemplary embodiment of the body portion, showing the location of small etch pits provided to discourage passage of fluid into the actuator cavity.

FIG. 17 shows further detail of the second exemplary embodiment 500 with additional features to discourage the flow of the fluid mixture along the rigid body 508 of microactuator 500. In FIG. 17, a plurality of shallow etch pits 509 may be formed in the rigid body 508. The number and placement of the etch pits 509 may depend on the surface tension of the fluid being used, and therefore may depend on the application. In the exemplary embodiment shown in FIG. 17, there are three etch pits placed about 3 μm apart, across the width of the rigid body 508. The edges of the apertures of the etch pits may be made sharp, with a small radius of curvature, to prevent the fluid meniscus from moving over or beyond these features. The etch pits may have an aperture of, for example, no more than about 1 μm long and 1 μm wide, to avoid etching the features through the thickness of the rigid body 508. Alternatively, the etch pits may extend through the entire thickness of rigid body 508, if the structural integrity of the rigid body 508 can support such a design. Otherwise, the etch pits may only extend to a certain depth as determined by the width and length of their apertures. A number of sets of such etch pits may be formed along the length of the rigid body 508, as shown in FIG. 17.

Either of microactuator 400 or microactuator 500 may be fabricated by deep reactive ion etching the appropriate pattern on the active layer of a silicon-on-insulator (SOI) substrate, after formation of the magnetizable portions of the microactuators 400 or 500. The silicon-on-insulator substrate may include a 625 μm silicon "handle" wafer, coated with a 1 μm thick layer of silicon dioxide, followed by a 50 μm "active" silicon layer. Details regarding the manufacturing and assembly processes of the optical layer 80, the actuator layer 100, and the manifold layer 90 may be found in U.S. Pat. No. 6,838,056 (the "'056 patent"), incorporated by reference herein in its entirety.

The magnetizable portions of the microactuators 400 and 500 may be made be depositing a thin metallic seed layer, such as chromium (Cr) and gold (Au) and depositing photoresist over the seed layer. The photoresist may then be patterned according to the shapes of the magnetizable features of microactuators 400 and 500. Finally, a magnetically permeable material with high saturation magnetization such as NiFe permalloy (70-80% Ni, 30-20% Fe) may be plated onto the patterned photoresist and seed layer, forming the magnetically permeable structures such as magnetizable portion 402 and 502, and motor poles 404, 504, 406 and 506. The photoresist and non-plated portions of the seed layer may then be removed, and the structure planarized by chemical mechanical polishing. An etch mask may subsequently cover the permalloy structures to avoid etching them during the formation of the remainder of the micromechanical actuator using deep reactive ion etching, for example, as described in the aforementioned '056 patent.

The manifold layer may also be fabricated from a silicon-on-insulator (SOI) wafer, with through holes etched into the "handle" of the SOI wafer. The buried oxide layer may then be removed, and the fluidic manifold features 93 and 110 patterned and etched into the "active" layer of the SOI, along with any bonding features and materials that are necessary to accomplish the bonding of the manifold wafer to the actuator and optical layers as described in the incorporated '056 patent.

Figure 18:
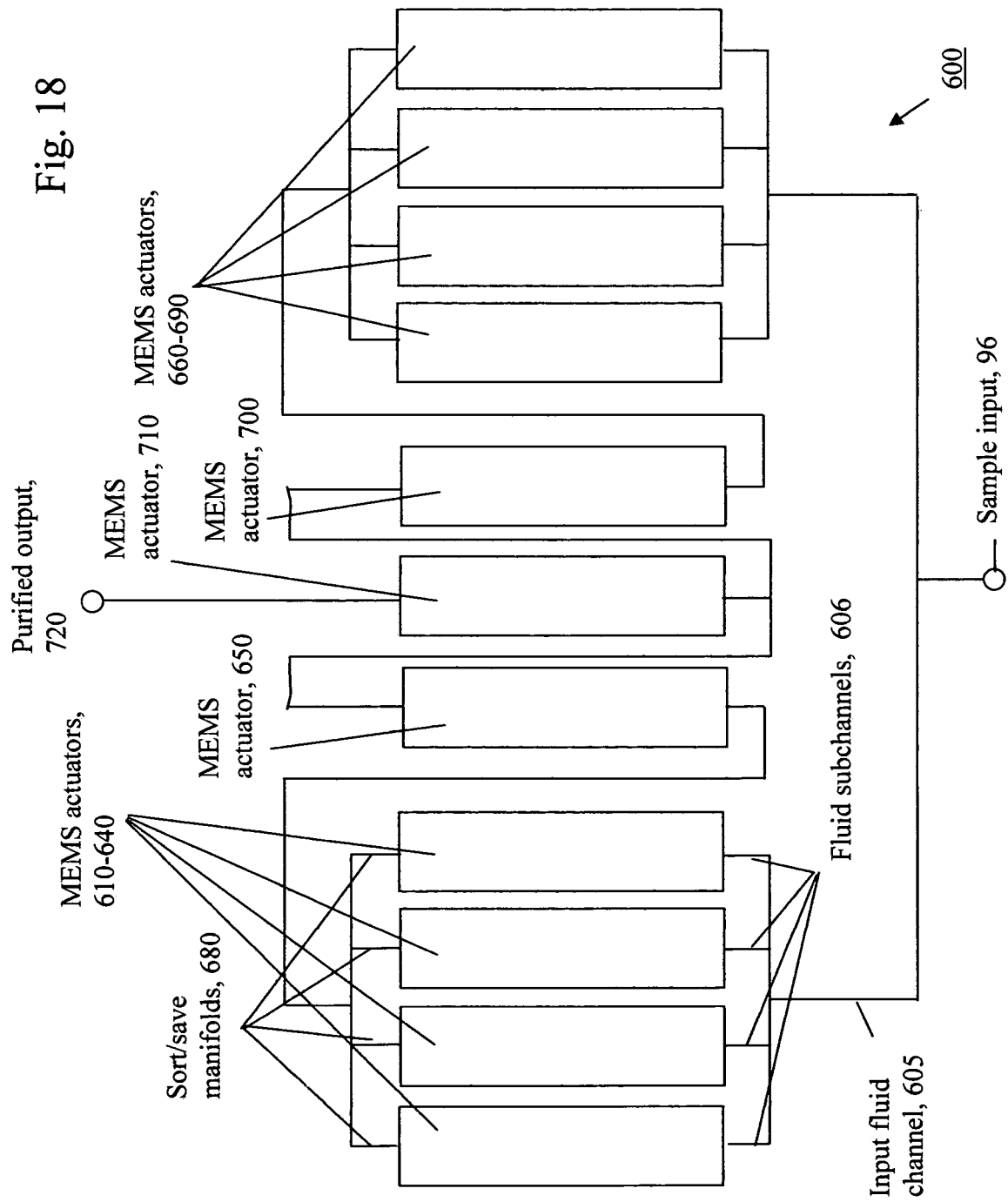
FIG. 18 is a schematic diagram of a plurality of MEMS actuators coupled to a single input stream in parallel, with the output of at least one MEMS actuator serving as the input to at least one other MEMS actuator.

While FIGS. 1 and 3 show each MEMS actuator being connected in parallel to the sample input 96 to maximize sorting speed, it should be understood that the MEMS actuators 192 may also be ganged or arranged partly in parallel, and partly serially, to accomplish other objectives. For example, FIG. 18 shows a 1×11 array of MEMS actuators, wherein two sets of four actuators each are coupled to a single input, such as sample input 96. The MEMS actuators 610-640 may be of the extensible/retractable type 400 or 500 shown in FIGS. 10 and 13, or the pivoting type 192 shown schematically in FIGS. 1 and 3, for example. The four fluid subchannels 606 couple the fluid from the input fluid channel 605 to each of the four MEMS actuators 610-640 in parallel. The output of each of MEMS actuators 610-650 is then combined in sort/save manifolds 680, and together are routed to the input of a fifth MEMS actuator 650. In this manner, MEMS actuator 650 sorts a fluid sample which has already been sorted by MEMS actuators 610-640. The output of MEMS actuator 650 may therefore be expected to be of higher purity than the output of any of MEMS actuators 610-640.

In a similar manner, the sample input 96 is coupled in parallel to the input manifolds of MEMS actuators 660-690. The sort/save output of MEMS actuators 660-690 is then combined as input to MEMS actuator 700. In this manner, MEMS actuator 700 sorts a fluid sample which has already been sorted by MEMS actuators 660-690. Therefore, the output of MEMS actuator 700 may be expected to be of higher purity than the output of any of MEMS actuators 660-690.

In a similar manner, the output of MEMS actuators 650 and 700 may be combined as input to a final MEMS actuator 710. This MEMS actuator 710 may produce the final, purified output 720.

Any number of variations of the configuration shown in FIG. 18 may be envisioned. For example, fewer or more MEMS actuators may be connected in parallel to determine the overall throughput of the device. Fewer or more MEMS actuators may then be connected in series to increase the sort purity of the output. Therefore, the arrangement of MEMS devices in series or in parallel will depend on the desired performance characteristics of the device, in terms of, for example, sort purity and throughput.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. While the embodiment described above relates to a microelectromechanical human hematopoietic stem cell sorter, it should be understood that the techniques and designs described above may be applied to any of a number of particle sorting applications. Other actuation means may be envisioned in addition to electromagnetic, including electrostatic, and fluidic. Particle sorting chips including n×m arrays of microelectromechanical actuators and parallel channels, as well as one-dimensional 1×m arrays of such microelectromechanical actuators and parallel channels are contemplated according to the systems and methods described here. Furthermore, details related to the specific design features of the microelectromechanical actuator and particle sorting chip are intended to be illustrative only, and the invention is not limited to such embodiments. Accordingly, the exemplary implementations set forth above, are intended to be illustrative, not limiting.

What is claimed is:

1. A micromechanical particle sorting apparatus comprising:
    at least one fluid channel defined at least partially in an optically transparent layer formed over a first substrate;
    at least one micromechanical actuator formed on the first substrate, which moves to direct a particle from a fluid stream at an outlet of the fluid channel, into one of a plurality of possible exit paths located in the first substrate; and
    at least one force-generating apparatus formed on a second surface which drives a motion in the at least one micromechanical actuator, wherein the second surface is separable from the first substrate.

2. The micromechanical particle sorting apparatus of claim 1, wherein the at least one force-generating apparatus generates magnetic flux, which drives the at least one micromechanical actuator.

3. The micromechanical particle sorting apparatus of claim 1, wherein the at least one micromechanical actuator includes at least one of a restoring spring, a crash stop and a damping plate which limit the motion of the micromechanical actuator.

4. The micromechanical particle sorting apparatus of claim 1, wherein the at least one micromechanical actuator includes a magnetizable portion coupled to a rigid body.

5. The micromechanical particle sorting apparatus of claim 4, further comprising at least one etch pit formed in the rigid body of the micromechanical actuator.

6. The micromechanical particle sorting apparatus of claim 1, wherein the at least one micromechanical actuator comprises at least one of an extensible/retractable type and a pivoting type.

7. The micromechanical particle sorting apparatus of claim 1, wherein the at least one micromechanical actuator includes at least one motor pole.

8. The micromechanical particle sorting apparatus of claim 1, wherein the first substrate is a silicon-on-insulator substrate.

9. The micromechanical particle sorting chip of claim 1, further comprising at least one second channel formed in a material adjacent to the optically transparent layer which directs the fluid stream from the at least one fluid channel in the optically transparent layer to the at least one micromechanical actuator.

10. The micromechanical particle sorting apparatus of claim 1, further comprising an input manifold and an output manifold coupled to the at least one micromechanical actuator, wherein the input manifolds of at least two micromechanical actuators are coupled together in a parallel arrangement.

11. The micromechanical particle sorting apparatus of claim 10, wherein an output of at least one micromechanical actuator provides an input to at least one other micromechanical actuator.

12. The micromechanical particle sorting apparatus of claim 1, wherein the at least one force-generating apparatus includes at least one magnetizable core wound with at least one turn of a conductive wire.

13. A method of manufacturing a micromechanical particle sorting apparatus, comprising:
    forming at least one fluid channel at least partially in an optically transparent layer formed over a first substrate;
    forming at least one micromechanical actuator on the first substrate which moves to direct a particle from a fluid stream at an outlet of the fluid channel into one of a plurality of possible exit paths located in the first substrate; and
    forming at least one force-generating apparatus on a second surface, which drives a motion in the at least one micromechanical actuator, wherein the second surface is separable from the first substrate.

14. The method of claim 13, wherein forming the at least one micromechanical actuator comprises forming at least one micromechanical actuator using photolithographic techniques on a silicon-on-insulator substrate.

15. The method of claim 13, further comprising forming at least one of a restoring spring, a crash stop and a damping plate on the micromechanical actuator.

16. The method of claim 13, further comprising forming at least one etch pit in the at least one micromechanical actuator.

17. The method of claim 13, further comprising:
    forming at least one second channel in a material adjacent to the optically transparent layer which directs the fluid stream from the at least one fluid channel in the optically transparent layer to the at least one micromechanical actuator.

18. The method of claim 13, wherein forming at least one force-generating apparatus includes forming at least one magnetizable core and winding the core with at least one turn of a conductive wire.

19. The method of claim 13, wherein forming the at least one micromechanical actuator comprises:
    forming at least one motor pole;
    forming a magnetizable portion which interacts with flux flowing in the motor pole; and
    coupling the magnetizable portion to a rigid body.

20. The method of claim 13, further comprising coupling an input of one micromechanical actuator and an input of at least one other micromechanical actuator to a fluid sample in a parallel arrangement.

21. The method of claim 13, further comprising coupling an output of at least one micromechanical actuator to an input of at least one other micromechanical actuator.

22. A method for sorting a particle from a fluid sample, comprising:
    supplying the fluid sample to a fluid channel formed at least partially in an optically transparent layer formed over a first substrate;
    applying laser light through the optically transparent layer to the particle in the fluid channel;
    detecting a fluorescence signal generated by the particle emitted through the optically transparent layer;
    activating a force-generating apparatus formed on a second surface in response to the detected fluorescence signal to drive a motion in at least one micromechanical actuator formed on the first substrate, wherein the second surface is separable from the first substrate; and moving the at least one micromechanical actuator to direct the particle into one of a plurality of possible exit paths formed in the first substrate.

23. The method of claim 22, further comprising:

limiting a motion of the at least one micromechanical actuator using at least one of a damping structure, a crash stop and a restoring spring, and a time varying force from the force-generating apparatus.

24. The method of claim 22, further comprising:

forming a presorted fluid stream by coupling one of the plurality of possible exit paths of a first micromechanical actuator to one of a plurality of possible exit paths from a second micromechanical actuator; and providing the presorted fluid stream as an input to a third micromechanical actuator.

* * * * *